(12) United States Patent
Allred et al.

(10) Patent No.: US 7,625,210 B2
(45) Date of Patent: *Dec. 1, 2009

(54) TREATMENT DEVICES FOR PROVIDING ORAL TREATMENTS AND KITS AND METHODS THAT UTILIZE SUCH TREATMENT DEVICES

(75) Inventors: Peter M. Allred, Riverton, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 624 days.

This patent is subject to a terminal disclaimer.

(21) Appl. No.: 10/914,487

(22) Filed: Aug. 9, 2004

(65) Prior Publication Data

US 2006/0029908 A1    Feb. 9, 2006

(51) Int. Cl.
*A61C 5/00*   (2006.01)
(52) U.S. Cl. .................................................. 433/215
(58) Field of Classification Search .................. 433/53, 433/215, 217.1
See application file for complete search history.

(56) References Cited

U.S. PATENT DOCUMENTS

| 165,584 | A | 7/1875 | Hopfen |
|---|---|---|---|
| 1,637,153 | A | 7/1927 | Lawton |
| 2,257,709 | A | 9/1941 | Anderson |
| 2,835,628 | A | 5/1958 | Saffir |
| 3,339,547 | A | 9/1967 | Drabkowski |
| 3,527,219 | A | 9/1970 | Greenberg |
| 3,577,640 | A | 5/1971 | Lee |
| 3,624,909 | A | 12/1971 | Greenberg |
| 3,688,406 | A | 9/1972 | Porter et al. |
| 3,955,281 | A | 5/1976 | Weitzman |
| 4,044,762 | A | 8/1977 | Jacobs |
| 4,063,552 | A | 12/1977 | Going et al. |

(Continued)

FOREIGN PATENT DOCUMENTS

WO    WO 88/06869    9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com.

(Continued)

*Primary Examiner*—John J Wilson
*Assistant Examiner*—Heidi M Eide
(74) *Attorney, Agent, or Firm*—Workman Nydegger

(57) ABSTRACT

Treatment devices in the shape of a dental tray, strip or patch include a barrier layer and a protective adhesive composition. Treatment kits include one or more treatment devices and one or more treatment compositions that are initially separate from the treatment devices. The treatment compositions may be contained within a syringe (e.g., a unit dose syringe) for ease of delivery. The treatment composition is dispensed from the syringe onto the barrier layer and then placed over a person's teeth and/or gums. The protective adhesive composition, in combination with the barrier layer, at least partially confines the treatment composition to a desired location within the person's mouth during use. The barrier layer protects the treatment and protective adhesive compositions from saliva or moisture found in the person's mouth.

38 Claims, 11 Drawing Sheets

U.S. PATENT DOCUMENTS

| | | | |
|---|---|---|---|
| 4,064,628 A | | 12/1977 | Weitzman |
| 4,138,814 A | | 2/1979 | Weitzman |
| RE33,093 E | | 10/1989 | Schiraldi et al. |
| 4,900,721 A | | 2/1990 | Bansemir et al. |
| 4,902,227 A | | 2/1990 | Smith |
| 4,965,618 A | * | 10/1990 | Devaney et al. ............ 396/605 |
| 5,008,093 A | | 4/1991 | Merianos |
| 5,051,476 A | | 9/1991 | Uji et al. |
| 5,085,585 A | | 2/1992 | Zimble |
| 5,108,742 A | | 4/1992 | Merianos |
| 5,112,225 A | | 5/1992 | Diesso |
| 5,183,901 A | | 2/1993 | Login et al. |
| 5,211,559 A | | 5/1993 | Hart et al. |
| 5,310,563 A | | 5/1994 | Curtis et al. |
| 5,326,685 A | | 7/1994 | Gaglio et al. |
| 5,346,061 A | | 9/1994 | Newman et al. |
| 5,356,291 A | | 10/1994 | Darnell |
| 5,376,006 A | | 12/1994 | Fischer |
| 5,425,953 A | | 6/1995 | Sintov et al. |
| 5,562,449 A | | 10/1996 | Jacobs et al. |
| 5,573,399 A | | 11/1996 | McClintock, II |
| 5,575,654 A | | 11/1996 | Fontenot |
| 5,611,687 A | | 3/1997 | Wagner |
| 5,616,027 A | | 4/1997 | Jacobs et al. |
| 5,631,000 A | | 5/1997 | Pellico |
| 5,639,445 A | | 6/1997 | Curtis et al. |
| 5,702,251 A | | 12/1997 | McClintock, II |
| 5,707,235 A | | 1/1998 | Knutson |
| 5,711,935 A | | 1/1998 | Hill et al. |
| 5,752,826 A | | 5/1998 | Andreiko |
| 5,769,633 A | | 6/1998 | Jacobs et al. |
| 5,816,802 A | | 10/1998 | Montgomery |
| 5,846,058 A | | 12/1998 | Fischer |
| 5,851,512 A | * | 12/1998 | Fischer ....................... 424/49 |
| 5,863,202 A | * | 1/1999 | Fontenot et al. ............. 433/215 |
| 5,879,691 A | | 3/1999 | Sagel et al. |
| 5,891,453 A | | 4/1999 | Sagel et al. |
| 5,894,017 A | | 4/1999 | Sagel et al. |
| 5,895,218 A | | 4/1999 | Quinn et al. |
| 5,916,653 A | * | 6/1999 | Kunstadter et al. ......... 428/42.1 |
| 5,922,307 A | | 7/1999 | Montgomery |
| 5,924,863 A | | 7/1999 | Jacobs et al. |
| 5,980,249 A | | 11/1999 | Fontenot |
| 5,985,249 A | | 11/1999 | Fischer |
| 5,989,569 A | | 11/1999 | Dirksing et al. |
| 6,036,943 A | | 3/2000 | Fischer |
| 6,045,811 A | | 4/2000 | Dirksing et al. |
| 6,080,397 A | | 6/2000 | Pfirrmann |
| 6,086,370 A | | 7/2000 | Jensen et al. |
| 6,089,869 A | | 7/2000 | Schwartz |
| 6,096,328 A | | 8/2000 | Sagel et al. |
| 6,106,293 A | | 8/2000 | Wiesel |
| 6,126,443 A | | 10/2000 | Burgio |
| 6,136,297 A | | 10/2000 | Sagel et al. |
| 6,142,780 A | | 11/2000 | Burgio |
| 6,155,832 A | | 12/2000 | Wiesel |
| 6,183,251 B1 | | 2/2001 | Fischer |
| 6,197,331 B1 | | 3/2001 | Lerner et al. |
| 6,247,930 B1 | | 6/2001 | Chiang et al. |
| 6,274,122 B1 | | 8/2001 | McLaughlin |
| 6,277,458 B1 | | 8/2001 | Dirksing et al. |
| 6,280,196 B1 | | 8/2001 | Berghash |
| 6,287,120 B1 | | 9/2001 | Wiesel |
| 6,306,370 B1 | | 10/2001 | Jensen et al. |
| 6,309,625 B1 | | 10/2001 | Jensen et al. |
| 6,312,671 B1 | | 11/2001 | Jensen et al. |
| 6,322,360 B1 | | 11/2001 | Burgio |
| 6,331,292 B1 | | 12/2001 | Montgomery |
| 6,343,932 B1 | | 2/2002 | Wiesel |
| 6,364,665 B1 | | 4/2002 | Trettenero |
| 6,379,147 B1 | | 4/2002 | Georgakis et al. |
| 6,419,903 B1 | | 7/2002 | Xu et al. |
| 6,419,906 B1 | | 7/2002 | Xu et al. |
| 6,435,873 B1 | | 8/2002 | Burgio |
| 6,440,396 B1 | | 8/2002 | McLaughlin |
| 6,458,380 B1 | | 10/2002 | Leaderman |
| 6,461,158 B1 | | 10/2002 | Sagel et al. |
| 6,488,914 B2 | | 12/2002 | Montgomery |
| 6,497,575 B2 | | 12/2002 | Zavitsanos et al. |
| 6,500,408 B2 | | 12/2002 | Chen |
| 6,503,486 B2 | | 1/2003 | Xu et al. |
| 6,506,053 B2 | | 1/2003 | Wiesel |
| 6,514,483 B2 | | 2/2003 | Xu et al. |
| 6,514,484 B2 | | 2/2003 | Rajaiah et al. |
| 6,551,579 B2 | | 4/2003 | Sagel et al. |
| 6,649,147 B1 | | 11/2003 | Ye et al. |
| 6,682,721 B2 | | 1/2004 | Kim et al. |
| 6,689,344 B2 | | 2/2004 | Chang et al. |
| 2001/0044096 A1 | * | 11/2001 | Lindquist ................... 433/215 |
| 2001/0046654 A1 | | 11/2001 | Zavitsanos et al. ............ 433/32 |
| 2002/0006387 A1 | | 1/2002 | Sagel et al. ................... 424/53 |
| 2002/0006388 A1 | | 1/2002 | Sagel et al. ................... 424/53 |
| 2002/0012685 A1 | | 1/2002 | Sagel et al. ................. 424/401 |
| 2002/0018754 A1 | | 2/2002 | Sagel et al. ................... 424/49 |
| 2002/0081555 A1 | | 6/2002 | Wiesel ...................... 433/215 |
| 2002/0164292 A1 | | 11/2002 | Peterson et al. ............... 424/53 |
| 2002/0182154 A1 | | 12/2002 | McLaughlin ................. 424/53 |
| 2002/0187111 A1 | | 12/2002 | Xu et al. ..................... 424/53 |
| 2002/0187112 A1 | | 12/2002 | Xu et al. ..................... 424/53 |
| 2003/0003421 A1 | | 1/2003 | Besenheider et al. ........ 433/215 |
| 2003/0012747 A1 | | 1/2003 | Peterson ..................... 424/53 |
| 2003/0036037 A1 | | 2/2003 | Zavitsanos et al. .......... 433/215 |
| 2003/0044631 A1 | | 3/2003 | Sagal et al. ................. 428/548 |
| 2003/0068284 A1 | | 4/2003 | Sagel et al. ................... 424/53 |
| 2003/0068601 A1 | | 4/2003 | Zavitsanos et al. .......... 433/215 |
| 2003/0082114 A1 | | 5/2003 | Kim et al. .................... 424/53 |
| 2003/0097122 A1 | * | 5/2003 | Ganz et al. ................. 433/215 |
| 2003/0133884 A1 | | 7/2003 | Chang et al. .................. 424/53 |
| 2003/0194382 A1 | | 10/2003 | Chang et al. .................. 424/53 |
| 2003/0198606 A1 | | 10/2003 | Kim et al. .................... 424/53 |
| 2005/0089819 A1 | | 4/2005 | Allred et al. |

FOREIGN PATENT DOCUMENTS

| | | |
|---|---|---|
| WO | WO 99/62472 | 12/1999 |
| WO | WO 03/000216 | 1/2003 |

OTHER PUBLICATIONS

Office Action dated Nov. 16, 2004 cited in U.S. Appl. No. 10/692,117.
Notice of Allowance dated Jun. 10, 2005 cited in U.S. Appl. No. 10/692,117.
Office Action dated Nov. 12, 2004 cited in U.S. Appl. No. 10/728,525.
Notice of Allowance dated Sep. 6, 2005 cited in U.S. Appl. No. 10/728,525.
Office Action dated Nov. 16, 2004 cited in U.S. Appl. No. 10/784,063.
Notice of Allowance dated Jun. 15, 2005 cited in U.S. Appl. No. 10/784,063.
Office Action dated Apr. 20, 2006 cited in U.S. Appl. No. 10/783,750.
Notice of Allowance dated Dec. 15, 2006 cited in U.S. Appl. No. 10/783,750.
Office Action dated Jul. 16, 2007 cited in U.S. Appl. No. 11/474,759.
Office Action dated Dec. 18, 2007 cited in U.S. Appl. No. 11/474,759.

* cited by examiner

TREATMENT DEVICES FOR PROVIDING ORAL TREATMENTS AND KITS AND METHODS THAT UTILIZE SUCH TREATMENT DEVICES

BACKGROUND OF THE INVENTION

1. The Field of the Invention

This invention is in the field of treatment devices, kits and methods for providing a desired treatment to a person's teeth and/or gums. More particularly, the invention relates to treatment devices that include a moisture-resistant barrier and a protective adhesive composition applied thereto, kits that employ such treatment devices and one or more syringes containing a treatment composition, and methods for their use.

2. The Relevant Technology

There is currently a wide variety of oral compositions used to provide a variety of different treatments to a person's teeth and/or gums. These include dental bleaching compositions, desensitizing compositions, remineralizing compositions, antimicrobial compositions, anti-plaque compositions, anti-tartar compositions, gingival soothing compositions, anesthetic compositions, anti-oxidant compositions, and mouth freshening compositions. A commonly used treatment composition is used in connection with dental bleaching.

Common bleaching methods typically involve the use of custom and non-custom dental trays. One type of custom tray is made from a stone cast of a person's teeth. Another is customized using a person's teeth as a template (e.g., "boil-and-bite" trays). Non-custom trays attempt to approximate the shape and size of a user's dental arch. An oral treatment composition is placed into the tray and the tray is placed over the person's teeth for a desired period of time.

Another bleaching method involves painting a bleaching composition directly onto a person's teeth. A perceived advantage of a paint-on bleaching composition is that it eliminates the need for a dental tray. A disadvantage of a paint-on bleaching composition is that it remains directly exposed to the person's saliva and disruptive forces found in the person's mouth. As a result, some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a polymer barrier that, at least in theory, keeps the dental bleaching gel from diffusing into the user's mouth.

Because of the generally poor adhesion of bleaching strips to the user's teeth, coupled with their generally flimsy nature, conventional bleaching strips are prone to slip off the teeth as a result of even minimal movement of the user's mouth, jaw or tongue. Indeed, it is recommended that the user not eat, drink, smoke or sleep while wearing the bleaching strip. Even if a user successfully maintains a conventional bleaching strip in its proper position the bleaching gel often diffuses into the person's saliva, potentially causing poor taste and possible discomfort to soft oral and throat tissues. Diffusion of the bleaching gel into the user's mouth can be accelerated by minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

What conventional dental trays, treatment strips and paint-on treatment composition have in common is a general inability to prevent diffusion of the treatment composition into a person's oral cavity. Except for dental splints or appliances that form a liquid tight seal against a person's teeth and/or gums, there is always some contact between the treatment composition and a person's saliva. The very presence of a dental tray, treatment strip or paint-on composition can cause increased salivation, as can diffusion of the treatment composition into the person's mouth, thereby providing even more saliva that can attack and diffuse the treatment composition into the person's oral cavity.

In view of the foregoing, there is a need for improved dental treatment apparatus that are simple and easy to use, that reliably remain in position over the user's teeth, and that can at least partially shield the treatment composition from saliva. Such improvements would be expected to improve or encourage user compliance.

BRIEF SUMMARY OF THE PREFERRED EMBODIMENTS

The present invention relates to treatment devices, kits and methods for providing a desired treatment to a person's teeth and/or gums. The treatment devices initially include a moisture resistant barrier layer and a protective adhesive composition pre-applied thereto. An initially separate treatment composition is applied to the barrier layer prior to use, typically by the user. The barrier layer protects both the treatment composition and protective adhesive composition from saliva found in a user's mouth during use. The protective adhesive composition is positioned so as to further shield the treatment composition from saliva, which, in combination with the barrier layer, further inhibits diffusion of the treatment composition into the user's mouth during use. The combination of the barrier layer and protective adhesive composition helps confine the treatment composition to a desired location in the user's mouth, which prevents, minimizes or lessens diffusion of the treatment composition into the user's oral cavity.

The barrier layer is advantageously formed from a moisture-resistant polymer material, examples of which include polyolefins, polyesters, ethylene-vinyl acetate copolymer (EVA), polyurethane, other polymers, and blends thereof. It may be in the form of a dental tray, strip, patch or other desired shape. The barrier layer is advantageously thin and flexible so as to conform to the shape of a person's dental arch as a result of the adhesive nature of the treatment and/or protective adhesive compositions. The barrier layer may be sufficiently sturdy and resilient as to assume and maintain a particular shape prior to, during, and after use. Alternatively, the barrier layer may formless so as to have no pre-defined shape prior to use (e.g., a strip or patch) such that it only conforms to the shape of a person's dental arch as a result of the adhesive action of the treatment composition and/or protective adhesive composition and/or by virtue of an external support (e.g., an exoskeleton, such as an external support tray). In a preferred embodiment, the barrier layer is reliably held in place over a user's teeth for a desired period of time by the adhesive action of the treatment and/or protective adhesive composition.

The size and shape of the barrier layer can be tailored to readily fit a person's upper or lower dental arch. They may also be tailored to fit persons having differently-sized or shaped dental arches. In one embodiment, the barrier layers are designed so as to substantially cover the front and lingual surfaces of the teeth and/or surrounding oral tissue to be treated. Treating both surfaces helps in treating the interproximal spaces between adjacent teeth.

Protective adhesive compositions according to the invention may comprise a gel or a substantially solid composition. They may comprise a bead, a continuous layer, or a plurality of discontinuous regions or islands. The protective adhesive composition can be formulated so as to be more viscous or less viscous than the treatment composition. It can be a gel or it can be substantially solid (e.g., a true solid or a highly viscous putty). In one embodiment, a substantially solid protective adhesive composition becomes more adhesive to teeth and/or soft oral tissue when moistened with saliva or water.

Protective adhesive compositions according to the invention generally include a tissue adhesion agent and, optionally, one or more liquid carriers into which the tissue adhesion agent is dispersed, one or more active agents, inert components, and adjuvents as desired. Whether the protective adhesive composition is a gel or is substantially solid largely depends on the relative concentrations of the tissue adhesion agent and the solvent or carrier. Increasing the ratio of solvent or carrier relative to the tissue adhesion agent generally decreases the viscosity of the composition, while decreasing the ratio of solvent or carrier relative to the tissue adhesion agent yields a composition having a greater viscosity. Further decreasing the concentration of the solvent or carrier at some point yields a composition that is so viscous as to be considered to be "substantially solid". In one embodiment, substantially solid protective adhesive compositions are manufactured by first forming a gel having a substantial quantity of a solvent and then removing some or all of the solvent by evaporation to yield a substantially solid composition. Some residual water or solvent may remain after removal of the solvent by evaporation.

In a preferred embodiment, the protective adhesive composition either includes no active agent(s) or a reduced amount of active agent(s) compared to the treatment composition. Including no, or a reduced quantity of, active agent results in a protective adhesive composition that reduces the likelihood that the active agent will diffuse into the user's oral cavity. In the case where the active agent is a dental bleaching agent, a protective adhesive composition that includes no, or a reduced quantity of, bleaching agent will generally be gentler on soft tissues compared to a treatment composition having a higher concentration of bleaching agent. In general, use of the protective adhesive composition generally allows the treatment composition to provide any desired concentration of active agent against a person's teeth and/or or surrounding oral tissues while confining the active agent in the desired location.

Treatment compositions according to the invention generally comprise one or more active agents, a tissue adhesion agent and, optionally, a liquid or gel solvent or carrier (e.g., in the case where the treatment composition is a gel), and other active agents, inert ingredients or adjuvents as desired. Treatment compositions according to the invention may also be in the form of a flowable gel or be substantially solid. Treatment compositions, particularly those that are substantially solid, can be formulated so as to become more adhesive to teeth when moistened with saliva or water during use. In the case where it is desired to dispense the treatment composition from a syringe, the treatment composition is preferably a flowable gel. Although syringe deliverable compositions can have any desired viscosity and/or stickiness, preferred gels according to the invention are generally thick and sticky so as to act as a highly viscous glue or adhesive that helps reliably maintain both the treatment composition and barrier layer against the person's teeth and/or surrounding oral tissue to be treated.

Kits according to the invention include one or more barrier layers to which a protective adhesive composition is pre-applied and one or more treatment compositions suitable for application to, or placement on, the barrier layer prior to use. According to one embodiment, a bead of a protective adhesive composition is pre-applied to an upper periphery or outer edge of the barrier layer, leaving a remaining space on the barrier layer for later placement of the treatment composition. According to another embodiment, two beads of protective adhesive composition are pre-applied to the barrier layer in a manner so as to at least partially surround a remaining space on the barrier layer for later placement of the treatment composition. The combination of a barrier layer and a protective adhesive composition may be referred to as a "treatment device", as may the combination of a barrier layer, protective adhesive composition, and treatment composition.

According to one embodiment, the treatment composition is preloaded within a syringe to facilitate dispensing of the treatment composition onto the barrier layer and/or directly onto the user's teeth or surrounding oral tissue by the user. In a preferred embodiment, one or more types of treatment composition are pre-loaded within unit dose syringes that deliver a pre-measured quantity of treatment composition onto the barrier layer. This helps prevent waste of the treatment composition and/or overdo sing by the user (e.g., in the case of a medicament composition that is harmful if ingested in larger quantities). In another embodiment, the treatment composition is pre-loaded within a multi-dose syringe that includes graduations that visually indicate individual dosages. According to another embodiment, the treatment composition is substantially solid (e.g., in the form of a pre-shaped tray insert or a roll of putty that can be separated into individual sections that can be placed against the barrier layer.)

In one embodiment, the barrier layer is in the shape of a dental tray having a front side wall, a rear side wall, and a trough between the front and rear side walls. Alternatively, the rear side wall may have cuts therein to further facilitate placement of the barrier layer and associated adhesive and treatment compositions over a person's teeth by minimizing the amount of manipulation necessary to obtain a good fit between the treatment device and the person's teeth. In the latter case, the barrier layer will still comprise a dental tray but it will not have a trough (i.e., the cuts within the rear side wall cause discontinuities that eliminate the existence of a "trough"). In another embodiment, the treatment devices are in the shape of strips or patches prior to use, being substantially flat and/or without front and rear side walls prior to use.

The kits can be designed to be used for any desired time period. In general, increasing the concentration of active agent within the treatment composition reduces the time required to effect a desired treatment. Treatment devices can be designed to be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional or overnight treatment while a person is sleeping, may last from about 2 hours to about 12 hours. Treatment sessions may be repeated as many times as are needed to obtain a desired degree of treatment. A typical treatment regimen will preferably include 1-20 treatment sessions, more preferably 2-15 treatment sessions, and most preferably 3-10 treatment sessions.

Treatment devices according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional bleaching strips, which do not reliably adhere to teeth, or intrusive treatment devices such as large, bulky dental appliances.

For convenience of use, multiple treatment devices comprising a barrier layer pre-loaded with a protective adhesive composition may be packaged together and sold as a kit, either alone but preferably in combination with one or more treatment compositions (e.g., loaded in a syringe). In one embodiment, the number of treatment devices provided with each kit may equal the number of sessions that represent a prescribed treatment regimen. To efficiently utilize the space within a kit package, multiple treatment devices can be stacked, internested, or laid together within a package. The treatment devices can be sealed collectively or individually as desired. They may contain a removable protective layer on their interior surfaces to protect the protective adhesive composition from contamination or moisture.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

I. Introduction and Definitions

Figure 1:
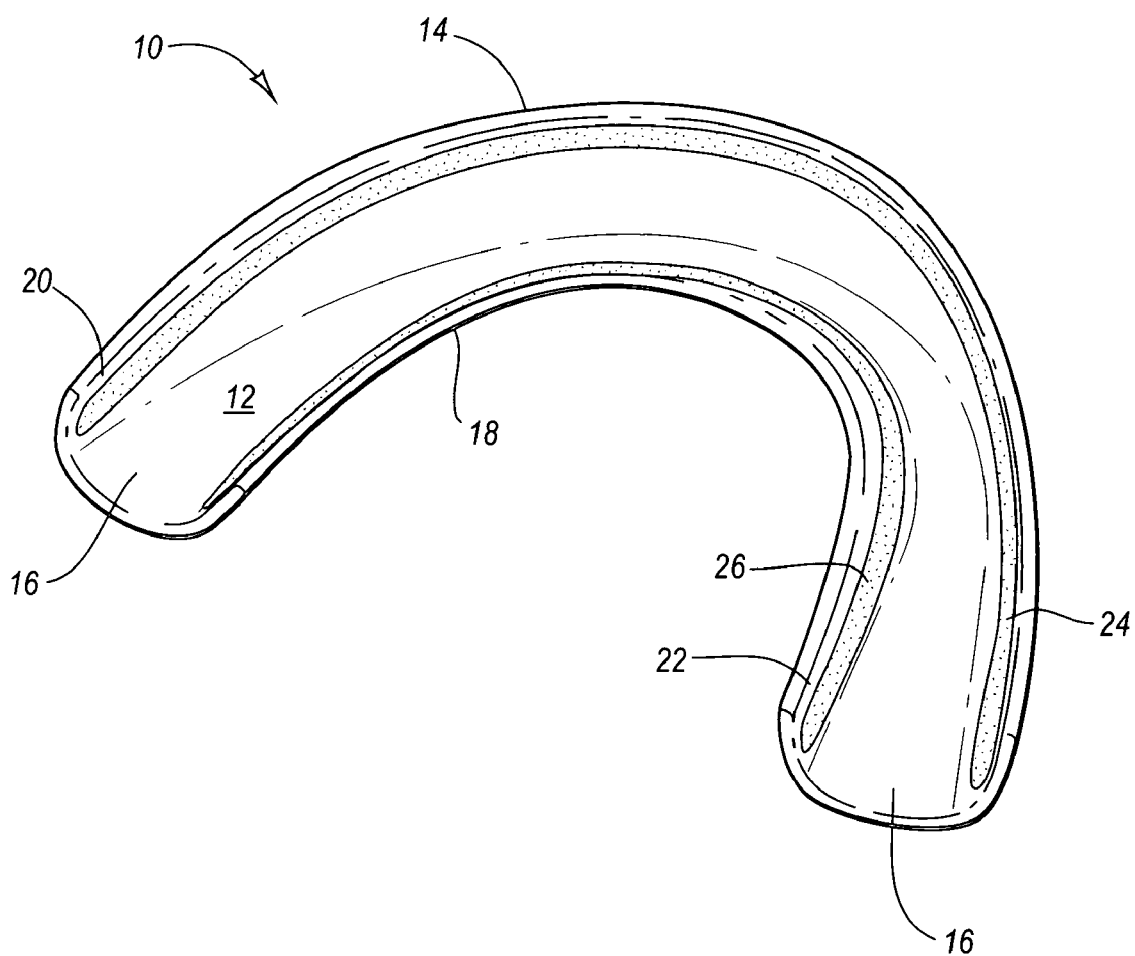
FIG. 1 is a perspective view of a treatment device comprising a barrier layer in the form of a dental tray and spaced-apart beads of a protective adhesive composition nearer the front and back rims.

The invention encompasses treatment devices, kits and methods for providing a desired treatment to a person's teeth and/or gums. The treatment devices initially include a protective adhesive composition pre-applied to a moisture resistant barrier layer. Kits include the treatment device and an initially separate treatment composition that is applied to the barrier layer prior to use. The barrier layer and protective adhesive composition work together to at least partially confine the treatment composition to a desired location in order to prevent, minimize or lessen diffusion of the treatment composition into the user's oral cavity. This, in turn, helps maintain the treatment composition in contact with a desired portion of the user's teeth and/or surrounding oral tissue to be treated.

The term "barrier layer", as used herein, refers to one or more layers of a material that protects the treatment composition and protective adhesive composition from ambient moisture and saliva found within a person's mouth when the treatment device is placed over the person's teeth and/or gums. The barrier layer may also serve to protect the protective adhesive composition from moisture and contaminants during storage and prior to use. The barrier layer may be in any desired form including, but not limited to, a dental tray, a tray-like shape, a strip or a patch. The terms "strip" and "patch" are essentially synonymous and refer to barrier layers and treatment devices that are essentially flat or formless prior to placing the treatment device over a person's teeth and/or gums.

The term "gel" shall refer to treatment and/or protective adhesive compositions that have been formulated or processed so as to be flowable, either by the force of gravity (i.e., having no yield stress) or that do not flow by the force of gravity but which are viscous or plastic such that they can be shaped or manipulated (e.g., they can be expressed from a syringe orifice or other dispensing means known in the art). The term "gel" broadly encompasses a wide range of compositions having greatly varying viscosities, although treatment and protective adhesive gels according to the invention are preferably sufficiently thick or viscous that they will not run out or off of a dental tray, tray-like device or other barrier layer by gravity alone. In one embodiment, the treatment and/or adhesive gel may be rubbery or highly viscous. At some point, when the viscosity becomes so great as to yield a composition that is substantially solid (e.g., a stiff or highly viscous putty), the composition may be considered to be "substantially solid".

The term "substantially solid", as used herein, refers to a treatment composition or protective adhesive composition or region that is in a solid or semi-solid condition. In one aspect, a "substantially solid" composition or region can be characterized as a cohesive mass that does not readily flow or separate when subjected to gravitational forces and which cannot be readily expressed through a syringe outlet or other similarly-sized opening or orifice. Thus, the term "substantially solid" excludes runny adhesive liquids, viscous adhesive liquids, and even thick adhesive gels that are able to flow when subjected to gravity and/or which can be readily expressed through a syringe outlet or other similarly-sized opening or orifice. The term "substantially solid", when used in the context of a treatment composition or protective adhesive composition, also excludes dry particulate compositions or powders because dry particulates and powders readily flow when subjected to gravity and/or are readily separated (i.e., the particles as a whole have little or no internal cohesion). Moreover, powders or particulates, when viewed as a whole, are not coherent or solid.

In one embodiment, the "substantially solid" compositions or regions become more adhesive when moistened with saliva or water. When moistened, the surface of the substantially solid composition or region turns into a sticky material that is able to more strongly adhere to teeth compared to a substantially solid composition or region that has not been moistened. The substantially solid composition may, at least on the surface, become a viscous liquid, paste or gel, at least temporarily, depending on the amount of moisture that is applied to the surface of the "substantially solid" composition or region. The consistency of the moistened surface can remain "substantially solid" depending on the degree of initial moistening, or it can stiffen and even revert back to being "substantially solid" as the initial quantity of surface moisture diffuses into a remaining portion of the "substantially solid" composition or region over time (e.g., during a treatment in which the composition is protected from saliva and ambient moisture in a person's mouth by a moisture-resistant barrier layer).

The term "dental tray", as used herein, refers to a treatment device having a tray-like shape so as to facilitate placement of the device over at least a portion of a person's dental arch. A "dental tray" or "tray-like" device includes a front side wall configured to engage front surfaces of a person's teeth and/or gums when in use, a rear side wall extending laterally from the front side wall, either abruptly by one or more distinct angles or non-abruptly by a curved transition portion, configured to engage lingual surfaces of the person's teeth and/or gums, and a trough between said front and rear side walls. A "dental tray" may be configured so that a portion of the front side wall, rear side wall, or a transition portion thereof (e.g., a bottom wall), engages the incisal or occlusal edges of the person's teeth when in use. The dental tray may be curved or straight in a longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space therebetween and are laterally offset by an angle of less than 180°. In practice, the front and rear side walls will be offset by an angle that is preferably less than about 150°, more preferably less than about 120°, and most preferably less than about 90°.

In the case where the front and rear side walls are connected by a transition portion (e.g., a trough having a U-shaped or rectangular cross section), at least a portion of the front and rear side walls may be substantially parallel (i.e., be offset by an angle of approximately 0°) or offset by a very small angle. In the case of a trough having a V-shaped or trapezoidal cross section, at least a portion of the front and rear side walls may be offset by an acute angle (i.e., by an angle between 0-90°). In the case of a trough having an L-shaped cross section, at least a portion of the front and rear side walls may be offset by an angle centered around approximately 90° (e.g., by an angle in a range of about 70° to about 110°). Thus, a trough having an L-shaped cross section can be a subset or slight variation of a trough having a V-shaped cross section.

Notwithstanding the foregoing, the bottom and/or rear side walls may have cuts therein to further facilitate placement of the barrier layer and associated adhesive and treatment compositions over a person's teeth by minimizing the amount of manipulation necessary to obtain a good fit between the treatment device and the person's teeth. In the latter case, the barrier layer will still comprise a dental tray but it will not have a trough (i.e., the cuts within the rear side wall cause discontinuities that eliminate the existence of a "trough").

The terms "longitudinal", "longitudinal dimension" and "longitudinal profile", as used herein when referring to a treatment device, shall refer to the lengthwise dimension of the device. The treatment device may be straight in the "longitudinal dimension" or it may be horseshoe-shaped or otherwise "longitudinally curved" in the longitudinal dimension so as to approximate the curvature of a person's dental arch, or at least facilitate placement of the treatment device over the dental arch.

The terms "strip" or "patch" are used interchangeably and shall refer to any barrier layer or treatment device that is substantially flat, or that only has a slight curvature or bend but that does not constitute a "dental tray", as that term is understood in the art. A "strip" or "patch", includes an inner surface or region generally oriented toward the front and/or rear surfaces of a person's teeth and/or gums when in use and an outer surface that is generally oriented away from the person's teeth and/or gums. A "strip" or "patch" may be configured so that a portion of the inner surface is oriented toward the incisal or occlusal edges of the person's teeth during use. The strip or patch may be curved or straight in one or both of the lengthwise and widthwise directions in order to fit over a user's teeth and/or gums in a desired manner.

The term "molecular weight", as used herein, shall refer to number average molecular weight expressed in Daltons, unless otherwise specified.

II. Treatment Devices

Treatment devices according to the invention include a barrier layer that protects a treatment composition and protective adhesive composition from ambient moisture within a person's mouth during use. Intermediate treatment devices include a barrier layer and a protective adhesive composition pre-applied to the barrier layer. Final treatment devices include a barrier layer, a protective adhesive composition, and a treatment composition, with the protective adhesive composition being positioned relative to the treatment composition in order to help confine the treatment composition to a desired location against a person's teeth and/or gums.

In one embodiment, the treatment composition is positioned adjacent to the barrier layer in a manner so as to contact one or both tooth surfaces to be bleached, and the protective adhesive composition is positioned adjacent to the barrier layer nearest the rim or edges of a treatment tray or strip so as to form an additional barrier that shields or protects the treatment composition from ambient moisture or saliva. One or both of the treatment composition and protective adhesive composition may be in gel form. Alternatively, one or both may be substantially solid. Following are preferred examples of barrier layers, protective adhesive compositions, and treatment compositions according to the invention, as well as characteristics of treatment devices made therefrom.

A. Barrier Layers

The barrier layer can have any desired shape or thickness. It is preferably moisture-resistant in order to protect the treatment and protective adhesive compositions from ambient moisture found in a person's mouth. According to one embodiment, the barrier layer comprises a thin, flexible membrane formed from a moisture-resistant polymer material. The barrier layer may comprise a conventional dental tray, examples of which include both customized and non-custom dental trays, or it may initially be a strip or patch, or have some other configuration.

Examples of materials that can be used to form the barrier layer include, but are not limited to, polyolefins, wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, or polyesteramides. Examples of suitable polyolefins that can be used to make the barrier layer include, but are not limited to, polyethylene (PE), high density polyethylene (HDPE), low density polyethylene (LDPE), ultra low density polyethylene (ULDPE), polypropylene (PP), and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by ArgoTech, which is located in Greenfield, Mass. The barrier layer may comprise a polymeric blend and/or multiple layers comprising two or more of the foregoing materials. Plasticizers, flow additives, and fillers known in the art can be used as desired to modify the properties of any of the foregoing polymers used to form the barrier layer.

According to one embodiment, the barrier layer is formed of a mixture of ethylene-vinyl acetate copolymer (EVA) and a polyolefin such as polyethylene (PE) or polypropylene (PP), preferably comprising about 5% to about 35% polyolefin, more preferably about 10% to about 30% polyolefin, more especially preferably about 15% to about 25% polyolefin, and most preferably about 18-20% polyolefin, with the balance comprising ethylene-vinyl acetate (EVA), and optionally other polymers and/or small quantities of additives such as plasticizers.

Other materials that can act as a barrier layer include cellulosic ethers, cellulose acetate, polyvinyl acetate, polyvinyl alcohol, shellac, and chemical or light-cure materials (e.g., methacrylate or acrylate resins). Examples of useful cellulosic ethers that can be used to form a barrier layer include, but are not limited to, ethyl cellulose, propyl cellulose, isopropyl cellulose, butyl cellulose, t-butyl cellulose, and the like.

In general, the thickness of the barrier layer can be selected to yield a treatment device having a desired level of strength, rigidity, resilience, and flexibility. In order for the barrier layer to be sufficiently flexible so as to conform to a person's teeth as result of adhesive action by the treatment composition and/or protective adhesive composition, the barrier layer will preferably have a thickness ranging from about 0.025 mm to about 1.5 mm, more preferably in a range of about 0.05 mm to about 1 mm, and most preferably in a range of about 0.1 mm to about 0.75 mm.

B. Protective Adhesive Composition

Protective adhesive compositions for use in making the inventive treatment devices and kits may have any desired consistency, such as being a flowable gel or being substantially solid and coherent. Protective adhesive compositions, when in the form of a gel, are preferably substantially viscous and tacky in order to help in retaining the treatment device against a person's teeth and/or gums during use. Protective adhesive compositions, when substantially solid, preferably become more adhesive to teeth and/or gums when moistened with water or saliva.

The protective adhesive composition may comprise a single mass or region, or it may comprise a plurality of masses or regions. Providing a protective adhesive composition better maintains the treatment composition in a desired location against the user's teeth and/or gums, as compared to treatment devices in the absence of the protective adhesive composition. This, in turn, promotes better treatment of the teeth and/or gums and patient compliance by, e.g., reducing irritation to surrounding oral tissues and/or at least some of the bad taste normally associated with treatment compositions.

In general, protective adhesive compositions will include at least one tissue adhesion agent. In the case where the protective adhesive composition is a gel, it will also include a liquid or gel solvent, carrier or vehicle into which the tissue adhesion agent is dispersed. The main difference between a composition that is a "gel" and one that is "substantially solid" is the level of solvent or carrier within the composition. In general, the greater the concentration of solvent or carrier relative to the tissue adhesion agent, the less viscous the gel. The lower the concentration of solvent or carrier relative to the tissue adhesion agent, the more viscous the gel. At some point, the ratio of solvent or carrier to tissue adhesion agent is low enough so that the composition is or becomes a stiff or highly viscous putty, which may be characterized as being "substantially solid". Stiff putties preferably become more adhesive to teeth when moistened with water or saliva. Substantially solid compositions can have so little solvent or carrier as to feel dry to the touch and be initially non-adhesive but then become adhesive to teeth when moistened with water or saliva. Substantially solid compositions can be made by initially including a very small amount of solvent or carrier and/or by first forming a flowable gel that is later dried to remove a substantial portion of the solvent or carrier.

The protective adhesive composition may optionally include one or more active agents (e.g., dental bleaching agents, desensitizing agents, remineralizing agents, antimicrobial agents, anti-plaque agents, anti-tartar agents, and the like), as well as one or more non-active ingredients (e.g., plasticizers, humectants, neutralizing agents, thickening agents, flavorants, sweeteners, and the like).

Exemplary protective adhesive compositions, as well as methods for manufacturing such compositions, which may be used to manufacture treatment devices according to the invention are disclosed in U.S. application Ser. No. 10/692,117, filed Oct. 22, 2003; U.S. application Ser. No. 10/728,525, filed Dec. 5, 2003; U.S. application Ser. No. 10/783,750, filed Feb. 19, 2004; and U.S. application Ser. No. 10/784,063, filed Feb. 19, 2004. For purposes of disclosing protective adhesive compositions and methods of making such compositions, the foregoing applications are incorporated herein by reference.

Following are preferred tissue adhesion agents, solvents or carriers, and other components within preferred protective adhesive compositions used to manufacture treatment devices and kits according to the invention.

1. Tissue Adhesion Agents

Useful tissue adhesion agents, which can also act as thickening agents that increase the viscosity of protective adhesive compositions and gels according to the invention, include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating protective adhesive compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the protective adhesive composition is a gel, the one or more tissue adhesion agents are preferably included in an amount in a range of about 1% to about 50% by weight of the protective adhesive gel, more preferably in a range of about 3% to about 30% by weight, and most preferably in a range of about 5% to about 20% by weight.

In the case where the protective adhesive composition is substantially solid, the one or more tissue adhesion agents are preferably included in an amount in a range of about 10% to about 90% by weight of the substantially solid adhesive composition, more preferably in a range of about 20% to about 80% by weight, and most preferably in a range of about 40% to about 75% by weight.

2. Carriers and Vehicles

Protective adhesive compositions for use in making treatment devices according to the invention, particularly gels, will typically include one or more liquid or gel solvents, carriers or vehicles into which the tissue adhesion agent and other components are dissolved or dispersed. Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

In the case of protective adhesive compositions that are substantially solid, the concentration of solvent, carrier or vehicle will typically be attenuated compared to protective adhesive gels. Where it is desired to form a protective adhesive gel that is later converted into a substantially solid protective adhesive composition, it may be advantageous to include one or more volatile solvents that can be removed by evaporation (e.g., water, alcohols, acetone, and other organic solvents). Because of the affinity of hydrophilic polymers for water, even protective adhesive compositions that appear to be solid may include a significant amount of bound water (e.g., up to about 10% or more by weight of the protective adhesive composition). In the case where the protective adhesive composition has the consistency of a highly viscous or stiff putty, the composition will generally include a solvent, carrier or vehicle that acts as a plasticizer or softening agent.

3. Other Components

The protective adhesive compositions may optionally include other components as desired to yield protective adhesive compositions having desired properties. Examples of "active" agents include, but are not limited to, dental bleaching agents (e.g., hydrogen peroxide, carbamide peroxide, sodium perborate, sodium percarbonate, and calcium peroxide), desensitizing agents (e.g., potassium nitrate, other potassium salts, citric acid, citrates, and sodium fluoride), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), gingival soothing agents (e.g., aloe vera, mild potassium nitrate, isotonic solution-forming salts (e.g., sodium chloride in an amount of about 0.9% by weight), and anesthetics (e.g., benzocaine, lidocain and the like)), antioxidants (e.g., vitamin A, vitamin C, vitamin E, other vitamins, chlorophyll and carotene), and other medicaments.

Examples of "non-active" agents include, but are not limited to, bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal pyrophosphates, alkyl sulfates, such as sodium lauryl sulfate, tin salts, such as sodium stannate, and tartrates), bleaching agent activators (e.g., bases, metals, metal compounds, and enzymes), neutralizing agents (e.g., sodium hydroxide and triethanolamine), colorants (e.g., carotene), preservatives (e.g., sodium benzoate, parabens, triclosan, phenols, chlorhexidine, and cetylpyridinium chloride), mouth freshening agents (e.g., camphor and wintergreen), inorganic thickening agents (e.g., fumed silica and fumed aluminum oxide), flavorants, sweeteners, and the like.

C. Treatment Compositions

Examples of treatment compositions for use with treatment devices and kits according to the invention include any known oral treatment composition. Examples include, but are not limited to, dental bleaching compositions, dental desensitizing compositions, remineralizing compositions, antimicrobial compositions, antiplaque compositions, and anti-tartar compositions.

Like the protective adhesive compositions discussed above, the treatment compositions may have any desired consistency. For example, the treatment composition may comprise a sticky viscous gel, a less viscous gel, a highly viscous putty, or a substantially solid adhesive composition that is less adhesive prior to being moistened with saliva or water but that becomes more sticky and adhesive when moistened. The treatment composition may comprise a single mass or region, or it may comprise a plurality of masses or regions.

In general, treatment compositions typically include at least one tissue adhesion agent, one or more active agents, and optionally one or more carriers and other adjuvents or additives. Following are examples of exemplary tissue adhesion agents, active agents, and other components.

1. Tissue Adhesion Agents

Useful tissue adhesion agents, which can also act as thickening agents that increase the viscosity of treatment compositions and gels according to the invention, include a wide variety of hydrophilic polymers. Examples of hydrophilic polymer tissue adhesion agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, and the like.

Non-limiting examples of polyvinyl pyrrolidone polymers that have been used in formulating treatment compositions according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million.

In the case where the treatment composition is a gel, the one or more tissue adhesion agents are preferably included in an amount in a range of about 1% to about 50% by weight of the treatment gel, more preferably in a range of about 3% to about 30% by weight, and most preferably in a range of about 5% to about 20% by weight.

In the case where the treatment composition is substantially solid, the one or more tissue adhesion agents are preferably included in an amount in a range of about 10% to about 90% by weight of the substantially solid treatment composition, more preferably in a range of about 20% to about 80% by weight, and most preferably in a range of about 40% to about 75% by weight.

2. Active Agents

In one embodiment, the active agent comprises at least one dental bleaching agent. A common dental bleaching agent that is known to bleach teeth and that has been found to be safe for oral use is hydrogen peroxide. However, hydrogen peroxide does not itself exist free in nature, but only as an aqueous solution or as a complex. Aqueous hydrogen peroxide is an acceptable dental bleaching agent to the extent that an anhydrous bleaching gel is not desired. Non-limiting examples of complexed hydrogen peroxide include carbamide peroxide and metal perborates. Other bleaching agents that can be used to bleach teeth include, but are not limited to, metal percarbonates, peroxides, chlorites, and hypochlorites, peroxy acids, and peroxy acid salts.

Bleaching agents within the treatment compositions according to the invention can have any desired concentration, e.g., between 1-90% by weight of the treatment composition. The concentration of the dental bleaching agent can be adjusted depending on the intended treatment time for each bleaching session. In general, the shorter the treatment time, the more bleaching agent will be added to accelerate dental bleaching so as to effect bleaching in a shorter time period.

In the case of a treatment composition used to bleach teeth, the one or more bleaching agents are preferably included in an amount in a range of about 1% to about 60% by weight of the treatment composition, more preferably in a range of about 3% to about 40% by weight of the treatment composition, and most preferably in a range of about 5% to about 30% by weight of the treatment composition.

Instead of, or an addition to a dental bleaching agent, the treatment compositions according to the invention may include one or more other active agents as desired to yield a treatment composition having desired properties. Examples of other active agents include desensitizing agents, antimicrobial agents, remineralizing agents, antiplaque agents, anti-tartar agents, and other medicaments known in the art.

Exemplary desensitizing agents for use in treating sensitive teeth include, but are not limited to, potassium nitrate, other potassium salts, citric acid, citrates, and sodium fluoride. When potassium nitrate is included within a treatment composition devoid of dental bleaching agents, it is preferably included in an amount in a range of about 0.01% to about 50% by weight of the treatment composition, more preferably in a range of about 0.1% to about 25% by weight of the treatment composition, and most preferably in a range of about 0.5% to about 10% by weight of the treatment composition.

When potassium nitrate is included in combination with a dental bleaching agent, the potassium nitrate is preferably included in an amount in a range of about 0.01% to about 2% by weight of the treatment composition, more preferably in a range of about 0.05% to about 1% by weight of the treatment composition, and most preferably in an amount of about 0.5% by weight of the treatment composition. It has been found that including potassium nitrate in these amounts creates a synergistic effect with the dental bleaching agent that appears to enhance tooth whitening. It also provides the highest level of tooth desensitization when used with a bleaching agent.

Exemplary antimicrobial agents that can be used to treat gingivitis, periodontal disease, plaque or other oral bacterial infections or maladies include, but are not limited to, chlorhexidine gluconate, cetylpyridinium chloride, phenol, minocycline, tetracycline, doxycycline, penicillin, clindamycin, ciprofloxacin, metronidazole, and tricolsan. When treating periodontal disease, chlorhexidine gluconate is a preferred medicament and is preferably included in an amount in a range of about 0.01 to about 50% by weight of the treatment composition, more preferably in a range of about 0.05% to about 25% by weight of the treatment composition, and most preferably in a range of about 0.1% to about 10% by weight of the treatment composition. Other anti-bacterial agents or medicaments may be included in the same concentration ranges.

Exemplary remineralizing agents capable of preventing caries include, but are not limited to, sodium fluoride, sodium monofluorophosphate, stannous fluoride, other fluoride salts, and calcium phosphate. Sodium fluoride can also act as a desensitizing agent. When used to remineralize teeth and prevent caries, the remineralizing agent is preferably included in an amount in a range of about 0.01 to about 20% by weight of the treatment composition, more preferably in a range of about 0.05% to about 10% by weight of the treatment composition, and most preferably in a range of about 0.1% to about 5% by weight of the treatment composition Exemplary anti-tartar agents include, but are not limited to, pyrophosphates, polypyrophosphates, polyvinyl methyl ether malic acid, sodium hexametal phosphate, alkali metal phosphates, calcium lactate, and triclosan.

Exemplary anticalculus or antiplaque agents include, but are not limited to, 8-hydroxyquinoline sulfate, dicitrate cyclic ester, and zinc citrate.

3. Carriers and Vehicles

Treatment compositions, particularly gels, will typically include one or more liquid or gel, solvents, carriers or vehicles into which the tissue adhesion agent, active agent(s), and other components are dissolved or dispersed. Examples of liquid or gel solvents, carriers or vehicles include, but are not limited to, water, alcohols (e.g., ethyl alcohol), and polyols (e.g., glycerin, sorbitol, mannitol, other sugar alcohols, propylene glycol, 1,3-propanediol, polyethylene glycol, polyethylene oxide, and polypropylene glycol).

In the case of treatment compositions that are substantially solid, the concentration of solvent, carrier or vehicle will typically be attenuated compared to treatment gels. Where it is desired to form a treatment gel that is later converted into a substantially solid treatment composition, it may be advantageous to include one or more volatile solvents that can be removed by evaporation (e.g., water, alcohols, acetone, and other organic solvents). Because of the affinity of hydrophilic polymers for water, even treatment compositions that appear to be solid may include a significant amount of bound water (e.g., up to about 10% or more by weight of the treatment composition). In the case where the treatment composition has the consistency of a highly viscous or stiff putty, the composition will generally include a solvent, carrier or vehicle that acts as a plasticizer or softening agent.

4. Other Components

The treatment compositions may optionally include other components as desired to yield treatment compositions having desired properties. Examples include, but are not limited to, gingival soothing agents (e.g., aloe vera, mild potassium nitrate, isotonic solution-forming salts (e.g., sodium chloride in an amount of about 0.9% by weight), and anesthetics (e.g., benzocaine, lidocain and the like), antioxidants (e.g., vitamin A, vitamin C, vitamin E, other vitamins, chlorophyll and carotene), bleaching agent stabilizers (e.g., EDTA, salts of EDTA, citric acid and its salts, phosphoric acid and its salts, phenolphosphonic acid and its salts, gluconic acid and its salts, alkali metal pyrophosphates, alkali metal pyrophosphates, alkyl sulfates, such as sodium lauryl sulfate, tin salts, such as sodium stannate, and tartrates), bleaching agent activators (e.g., bases, metals, metal compounds, and enzymes), neutralizing agents (e.g., sodium hydroxide and triethanolamine), colorants (e.g., carotene), preservatives (e.g., sodium benzoate, parabens, triclosan, phenols, chlorhexidine, and cetylpyridinium chloride), mouth freshening agents (e.g., camphor and wintergreen), inorganic thickening agents (e.g., fumed silica and fumed aluminum oxide), flavorants, sweeteners, and the like.

D. Optional Exoskeleton Support Tray

It is within the scope of the invention to utilize an exoskeleton support tray, which can be used to facilitate placement of the treatment device into a person's mouth. In the case where the treatment device is very flexible, the exoskeleton support tray may also help maintain the treatment device in a desired shape (e.g., in the shape of a tray) prior to use. The exoskeleton support tray may comprise any material (e.g., polymers, foil, cardboard, or laminates), including one or more materials disclosed above with respect to the barrier layer.

Exemplary exoskeleton support trays for use in combination with a barrier layer are disclosed in U.S. application Ser. No. 10/444,242, filed May 23, 2003 and U.S. application Ser. No. 10/783,597, filed Feb. 19, 2004. For purposes of disclosing exoskeleton support trays for use in combination with a barrier layer, particularly barrier layers having certain materials properties and/or shapes, the foregoing applications are incorporated by reference.

According to one embodiment, it may be desirable to include a releasable adhesive that temporarily adheres the exoskeleton support tray and treatment tray together prior to use. Examples include viscous or semi-viscous liquids. Even static cling between the exoskeleton support tray and treatment tray may provide this function.

E. Characteristics of Oral Treatment Devices

In one embodiment, oral treatment devices according to the invention are in the shape of a dental tray having a front side wall, a rear side wall, and an interior volume between the front and rear side walls. Having the shape of a dental tray facilitates placement of the treatment device over a person's teeth by reducing the amount of manipulation necessary to obtain a good fit between the device and the person's teeth. In another embodiment, the treatment devices are in the shape of a patch or strip. It is within the scope of the invention for the treatment devices to have any desired shape or configuration. In contrast to conventional bleaching strips, which are not recommended for use while a person eats, drinks, smokes or sleeps, treatment devices according to the invention can be designed so as to be worn while talking, sleeping, eating, drinking, smiling, frowning, grimacing, yawning, coughing, smoking, or making virtually any facial expression or mouth contortion.

According to one embodiment, the treatment device has a horseshoe shaped longitudinal profile and a trough with a U-shaped cross section, much like a conventional dental tray. One exemplary treatment device in the form of a dental tray is depicted in FIGS. 1-4. FIG. 1 is a perspective view of a treatment device 10 that includes a barrier layer 12 (preferably comprising a moisture-resistant material) having a front side wall 14, a bottom wall 16, and a rear side wall 18 that together define a barrier layer that is generally horseshoe-shaped in a longitudinal dimension and that has a generally U-shaped cross section defining an interior volume. The cross section of the barrier layer 12 near the incisors is seen more clearly in FIG. 4.

The front side wall 14 of the barrier layer 12 further includes a front rim 20, and the rear side wall of the barrier layer 12 further includes a back rim 22. In one embodiment, one or both of the front and back rims 20, 22 of the barrier layer 12 are designed so as to terminate at or shy of the gingival margin when the treatment device 10 is in use. In another embodiment, one or both of the front and back rims 20, 22 of the barrier layer are designed so as to extend beyond the gingival margin and partially overlap the person's gums when the treatment device 10 is in use.

As seen in FIG. 1, a first protective adhesive composition 24 is positioned adjacent to the front rim 20, and a second protective adhesive composition 26 is positioned adjacent to the back rim 22. According to this embodiment, there exists a space between the first and second protective adhesive compositions 24 and 26 within the interior volume of the barrier layer 12 into which a treatment composition can be placed prior to use.

Figure 2:
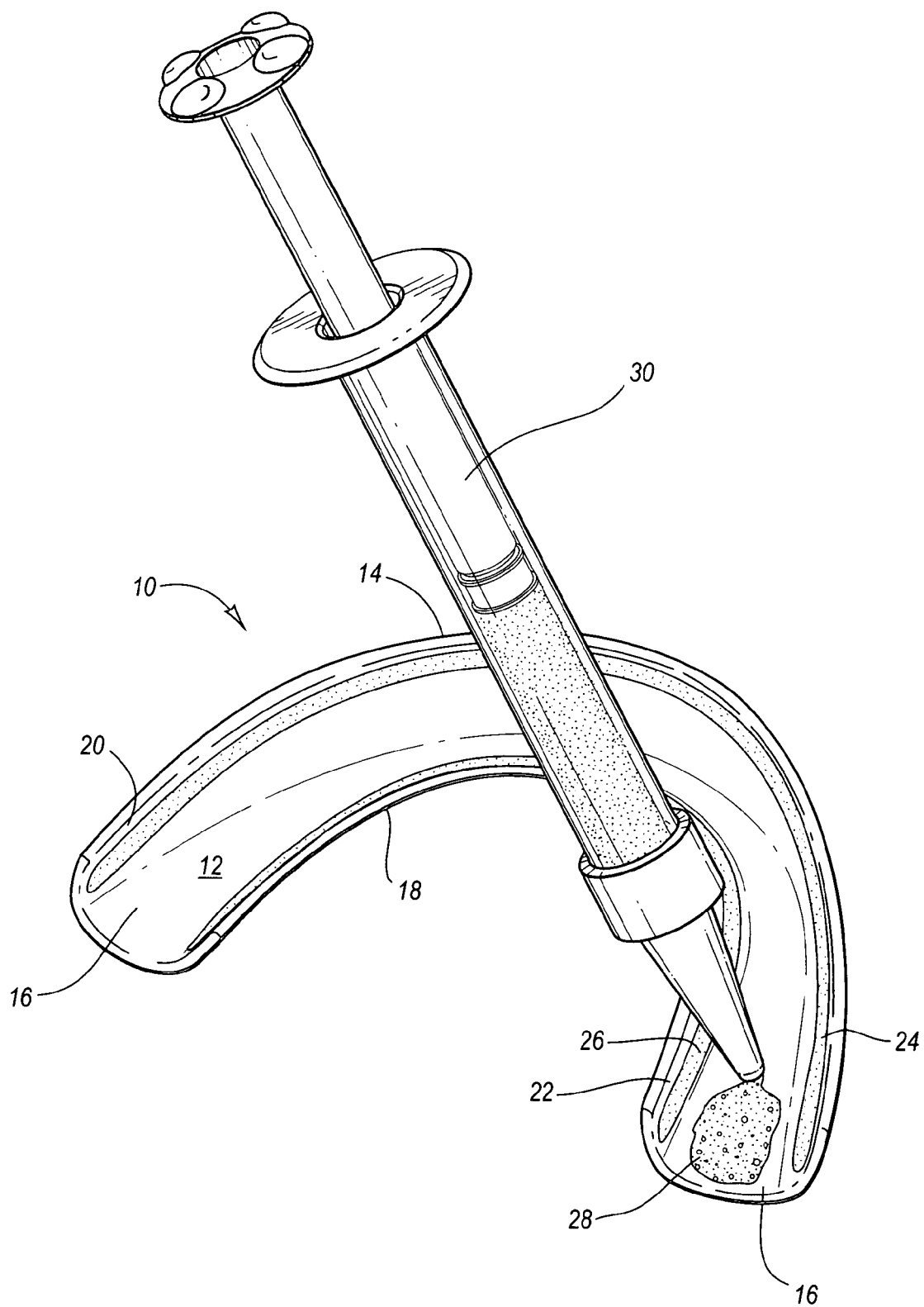
FIG. 2 illustrates a treatment composition being applied to the treatment device of FIG. 1 between the beads of protective adhesive composition using a unit dose syringe.

FIG. 2 shows a treatment composition 28 being placed into the space between the first and second protective adhesive compositions 24 and 26 within the interior volume of the barrier layer 12. According to this embodiment, the treatment composition 28 is dispensed from a syringe 30 (e.g., a unit dose syringe as shown in FIG. 2 or a syringe that includes multiple doses of the treatment composition). The advantage of using a unit dose syringe is that a pre-determined amount of the treatment composition can be placed into the syringe, thereby preventing accidental overdose or the use of an incorrect amount of the treatment composition 28. It will be appreciated that any dispensing device can be used. In addition, a substantially solid treatment composition in the form of an insert or putty can be placed into the interior volume of the barrier layer 12.

Figure 3:
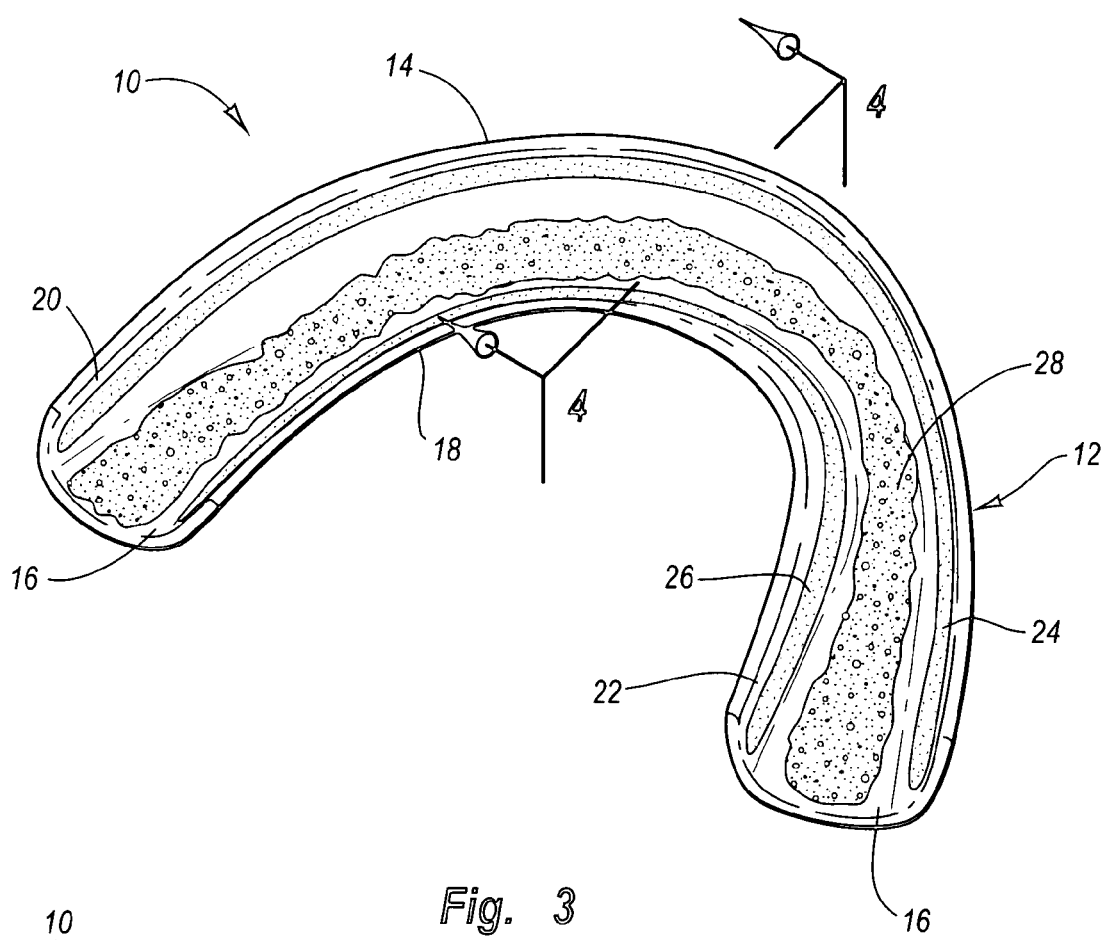
FIG. 3 illustrates the treatment device of FIG. 1 after placement of the treatment composition between the beads of protective adhesive composition.
Figure 4:
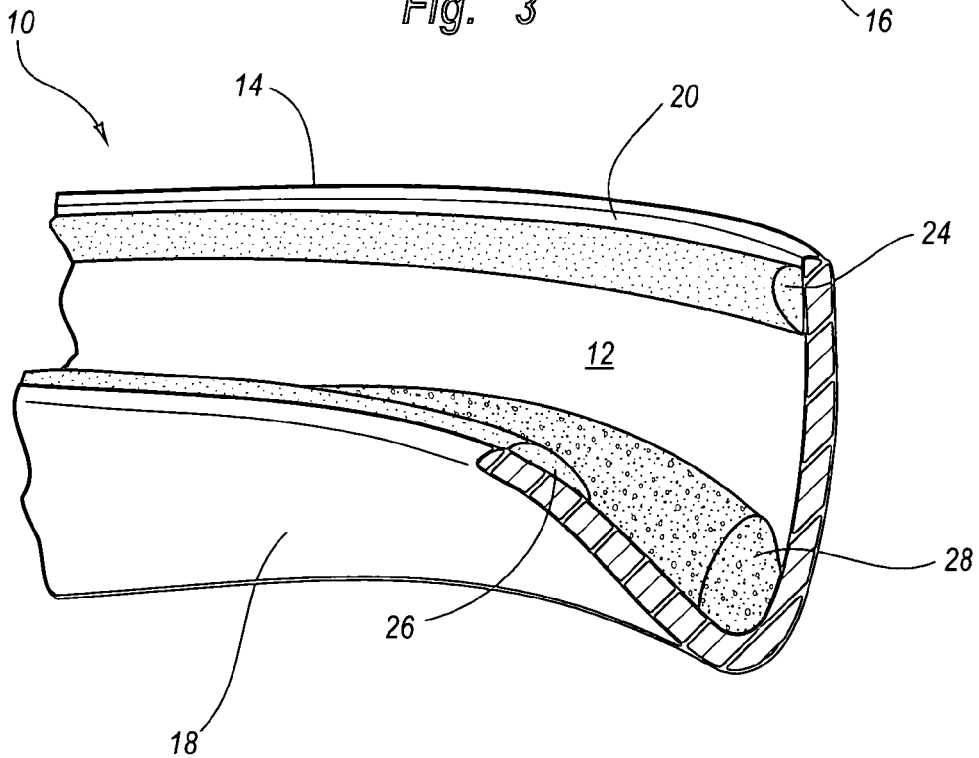
FIG. 4 is a cross-sectional view of the treatment device shown in FIG. 3.

FIG. 3 shows the treatment device 10 after having introduced the treatment composition 28 into the interior volume of the barrier layer 12 prior to use. FIG. 4 is cross sectional view of the treatment device 10 shown in FIG. 3. As shown in FIGS. 3 and 4, the treatment composition 28 is positioned in the space between the first and second protective adhesive compositions 24 and 26. During use, the first and second protective adhesive compositions 24 and 26, in combination with the barrier layer, help confine the treatment composition 28 to a desired location against a person's teeth and/or gums (e.g., FIG. 6). For example, in the case where the treatment composition 28 is a bleaching composition, desensitizing composition, a remineralizing composition, or other dental composition, the first and second protective adhesive compositions 24 and 26 can act to confine the treatment composition 28 so as to primarily or exclusively contact the labial and lingual tooth surfaces of the teeth being treated.

Figure 5:
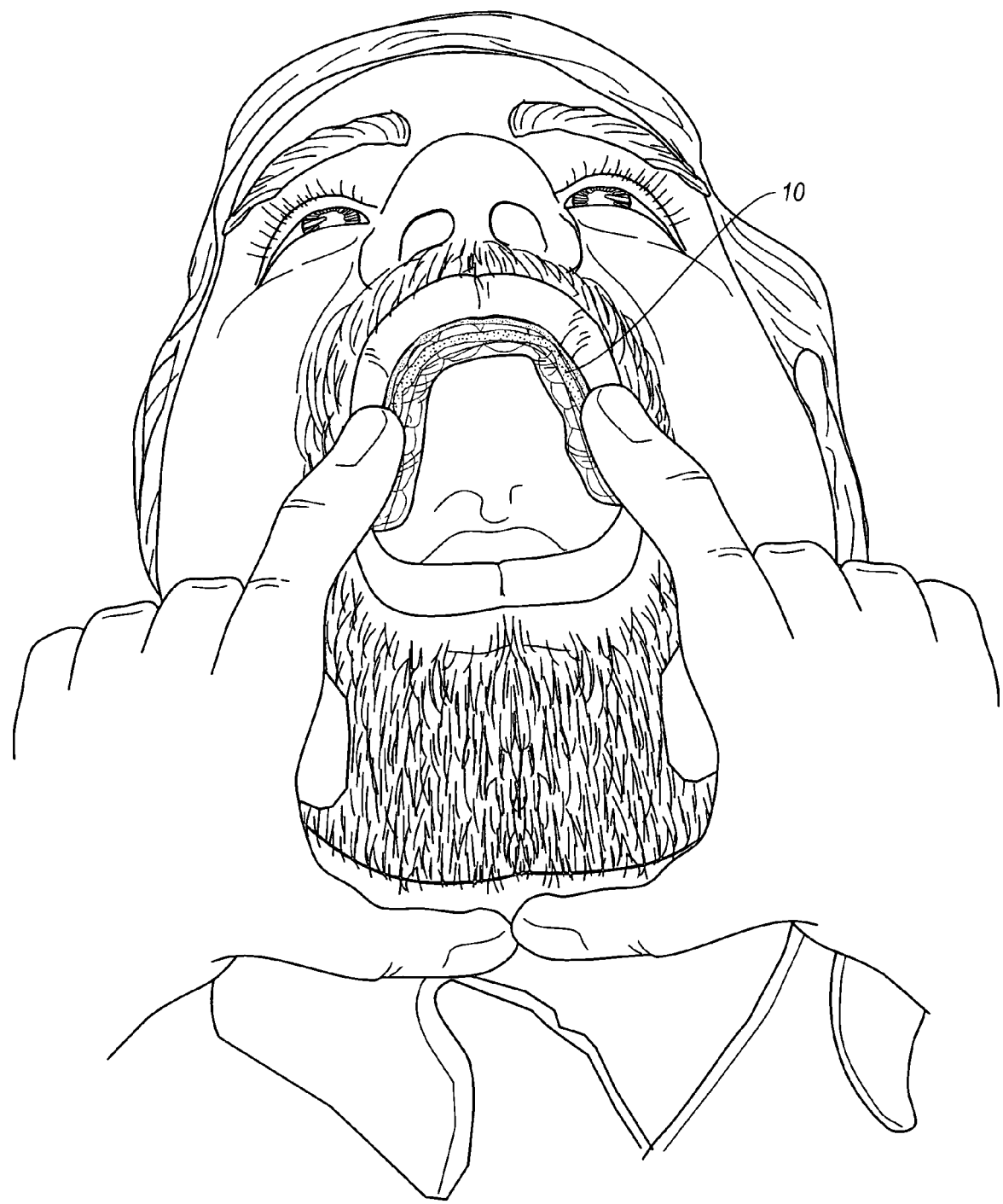
FIG. 5 illustrates a person installing the treatment device of FIG. 3 over the person's teeth and adjacent gingival tissue.
Figure 6:
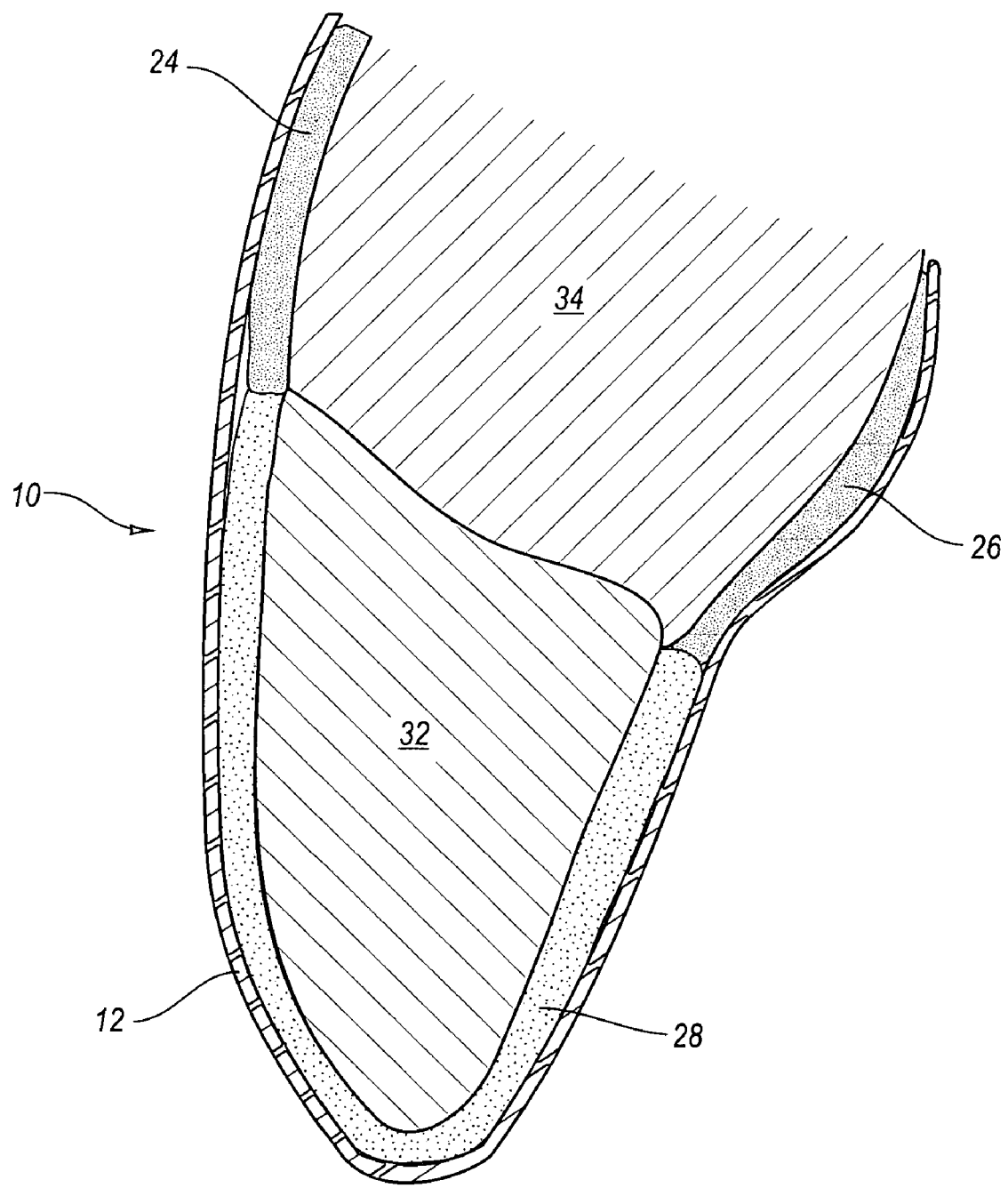
FIG. 6 is a cross-sectional view of a tooth being treated with a treatment composition positioned on the labial and lingual surfaces of the tooth, a protective adhesive composition positioned over the gingival margins and adjacent gingival tissue, and a barrier layer placed over the treatment composition and protective composition.

FIG. 5 shows the treatment device 10 being placed over a person's teeth as part of a desired treatment. FIG. 6 is a cross sectional view showing the treatment device 10 covering the labial and lingual surfaces of a tooth 32 and also overlapping the labial and lingual surfaces of adjacent gingival tissue or gum 34. The treatment composition 28 is positioned over the labial and lingual surfaces of the tooth 32. The first protective adhesive composition 24 is positioned at the labial gingival margin and extends over at least a portion of the labial surface of the person's gum 34. The second protective adhesive composition 26 is positioned at the lingual gingival margin and extends over at least a portion of the lingual surface of the person's gum 34. In this way, the first and second protective adhesive compositions 24 and 26 help confine the treatment composition 28 so as to remain in contact with the tooth 32. In addition, the first and second protective adhesive compositions 24 and 26 help protect the gingival tissue 34 from any soft tissue irritants that may be contained within the treatment composition (e.g., dental bleaching agents).

Figure 7:
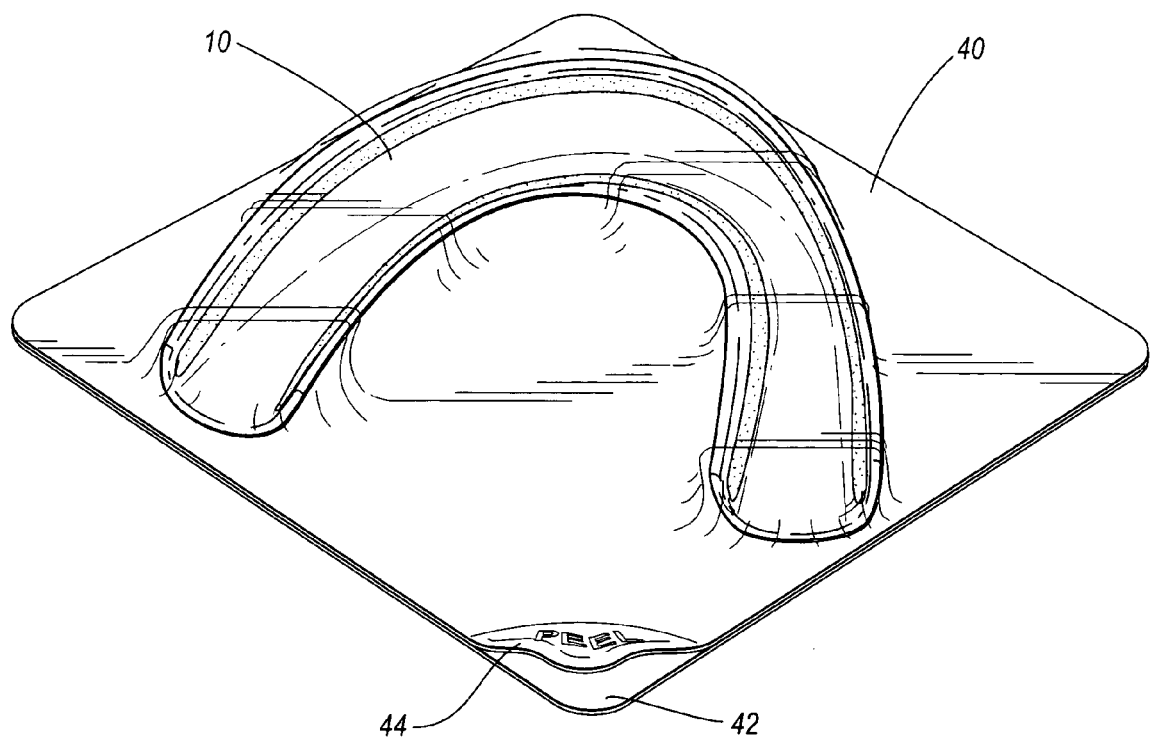
FIG. 7 illustrates a treatment device according to the invention contained within a sealed protective package having a peelable cover.

In order to protect treatment devices according to the invention from contaminants during storage and prior to use, the treatment devices can be packaged within a sealed container or package. As illustrated in FIG. 7, a treatment device 10 according to the invention can be sealed within a protective package 40 that includes a rigid support layer 42 and a peelable cover 44. When it is desired to use the treatment device 10, the peelable cover 44 is removed and the treatment device 10 is removed or separated from the support layer 42.

In one embodiment, the support layer 42 includes a shaped portion that acts as exoskeleton to hold or maintain the treatment device 10 in the shape of a dental tray or other desired configuration prior to use. In use, both the treatment device 10 and support layer 42 can be placed into a person's mouth so as to initially position the treatment device 42 over the person's teeth and/or gums. Thereafter, the support layer 42 is removed, leaving only the treatment device 10 within the person's mouth. This permits further manipulation of the barrier layer 12 in order for the treatment device 10 to better conform to the shape of the person's dental arch and/or irregularities of the person's teeth.

In addition to, or instead of, the protective package 40, the treatment device may alternatively include a removable protective layer (not shown) that is temporarily placed within the interior volume adjacent to the protective adhesive composition. When it is desired to use the treatment device, the removable protective layer is removed so as to expose the protective adhesive composition.

Figure 8:
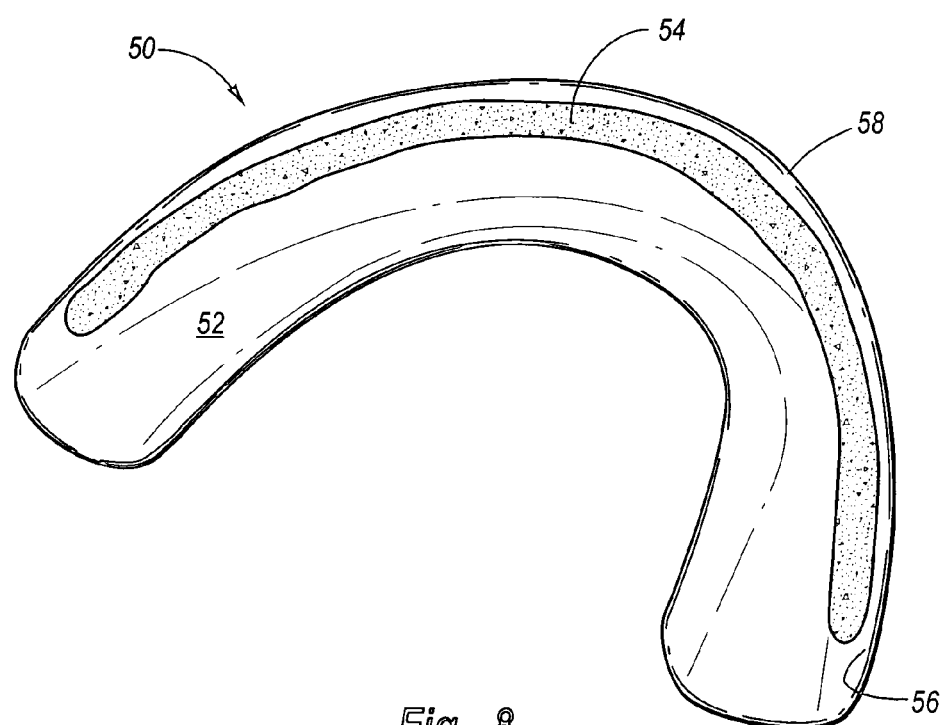
FIG. 8 is a perspective view of an exemplary treatment device comprising a single bead of a protective adhesive composition adjacent to the front rim of a dental tray.

FIG. 8 depicts an alternative treatment device 50 having a barrier layer 52 in the form of a tray and a single bead or strip of a protective adhesive composition 54 adjacent to an upper rim 56 of a front side wall 58. This embodiment is useful in the case where the treatment composition (not shown) is intended to only contact the labial surfaces of a person's teeth and/or gums.

Figure 9:
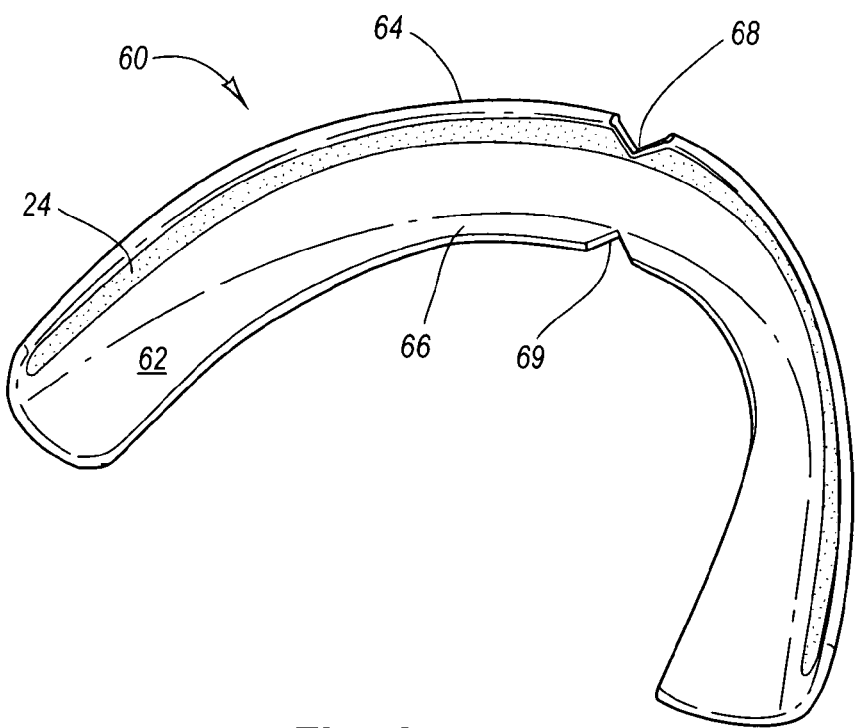
FIG. 9 is a perspective view of an exemplary treatment device having an L-shaped trough, a curved longitudinal profile, and notches in the rims.

FIG. 9 illustrates an alternative embodiment of a treatment device 60 according to the invention that has an L-shaped cross section. More particularly, the treatment device 60 includes a barrier layer 62 having front side wall 64 and a rear side wall 66 extending laterally from the front side wall 64 so that the barrier layer 62 has an approximate L-shaped cross section. The L-shaped treatment device 60 of FIG. 9 is somewhat easier to initially place over a person's dental arch compared to the U-shaped treatment devices of FIGS. 1-4. This is due to the approximately planar orientation of the rear side wall 66 relative to the occlusal or incisal edges of a person's teeth when the front side wall 64 of the treatment device 60 is initially placed and adhered against the front surfaces of a person's teeth. On the other hand, more manipulation of the L-shaped treatment device 60 is generally required to form and adhere the rear side wall 66 against the lingual surfaces of the person's teeth as a result of the greater initial offset angle between the front side wall 64 and rear side wall 66.

In the case of the treatment device 60 having an L-shaped cross section, it may be more correct to say that the rear side wall 66 extending laterally from the front side wall 64 is really a bottom wall rather than a rear side wall. Nevertheless, because this erstwhile "bottom wall" of the L-shaped treatment device 60 is folded back against the lingual tooth surfaces during use, it can be readily seen that a treatment device having an L-shaped trough is merely a variation of a treatment device having a U- or V-shaped trough. Thus, for purposes of this disclosure and the appended claims, the side wall 66 shall constitute, and fall within the definition of, a "rear side wall".

To facilitate the ability of a treatment device to conform to the varying shapes and sizes among dental arches, the treatment device may include mechanical features such as one or more notches within the front or rear side walls. As also shown in FIG. 9, the treatment device 60 further includes a notch 68 near the center of the rim of the front side wall 64 and a notch 69 near the center of the rim of the rear side wall 66. Notches 68 and 69 allow the tray-like treatment device 60 to more easily spread open or compress when being conformed to differently-sized dental arches. In this way, the treatment device 60 can more easily be "one-size fits all".

Figure 10:
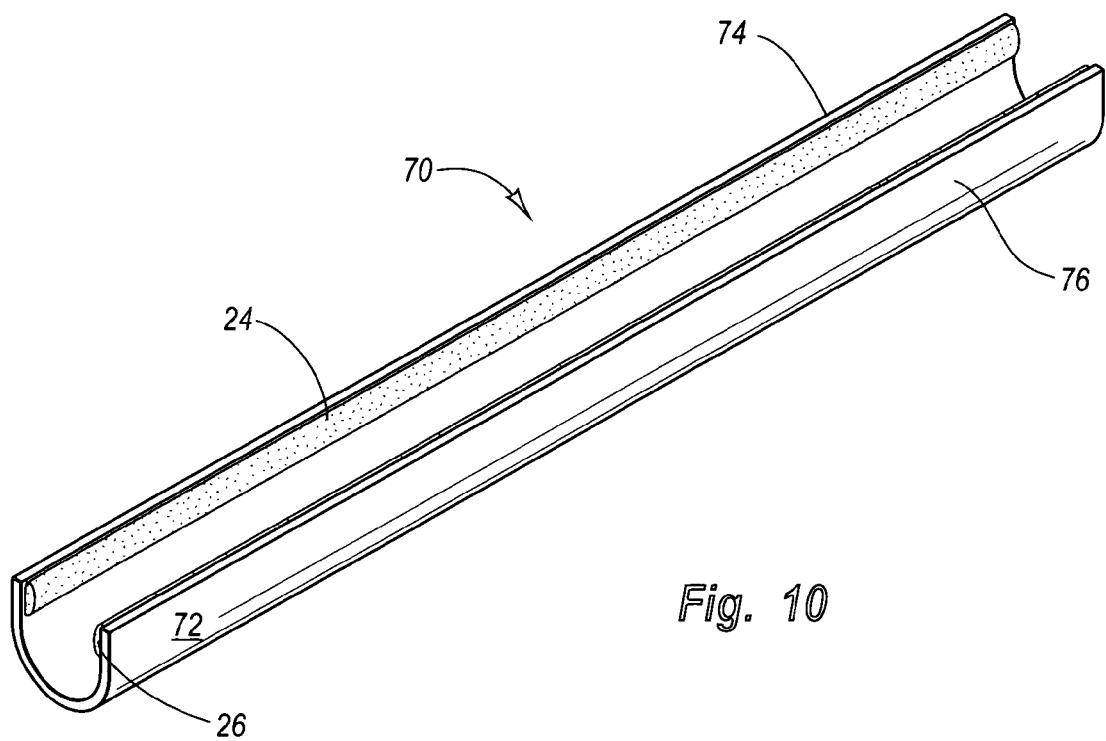
FIG. 10 is a perspective view of an exemplary treatment device having a U-shaped trough and a substantially straight longitudinal profile.

FIG. 10 depicts an alternative embodiment of a treatment device 70 according to the invention, which includes a barrier layer 72 having a front side wall 74, a rear side wall 76, and a U-shaped cross section. Instead of being horseshoe shaped, or otherwise having a curved longitudinal profile, the treatment device 70 of FIG. 10 has a substantially straight or linear longitudinal profile.

Figure 11:
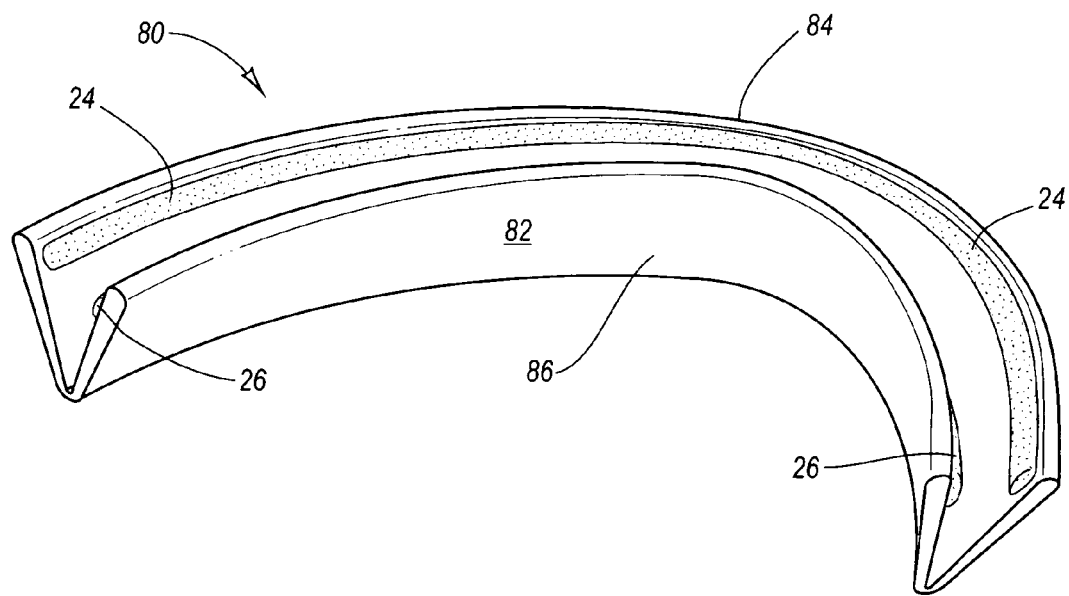
FIG. 11 is a perspective view of an exemplary treatment device having a V-shaped trough and a curved longitudinal profile.

FIG. 11 depicts yet another alternative embodiment of a treatment device 80 according to the invention. The treatment device 80 includes barrier layer 82 having a front side wall 84, a rear side wall 86, a V-shaped cross section, and a curved longitudinal profile. The main difference between the V-shaped treatment device 80 of FIG. 11 and the L-shaped treatment device 60 of FIG. 9 is the angle at which the front and rear side walls are laterally offset from each other.

Figure 12:
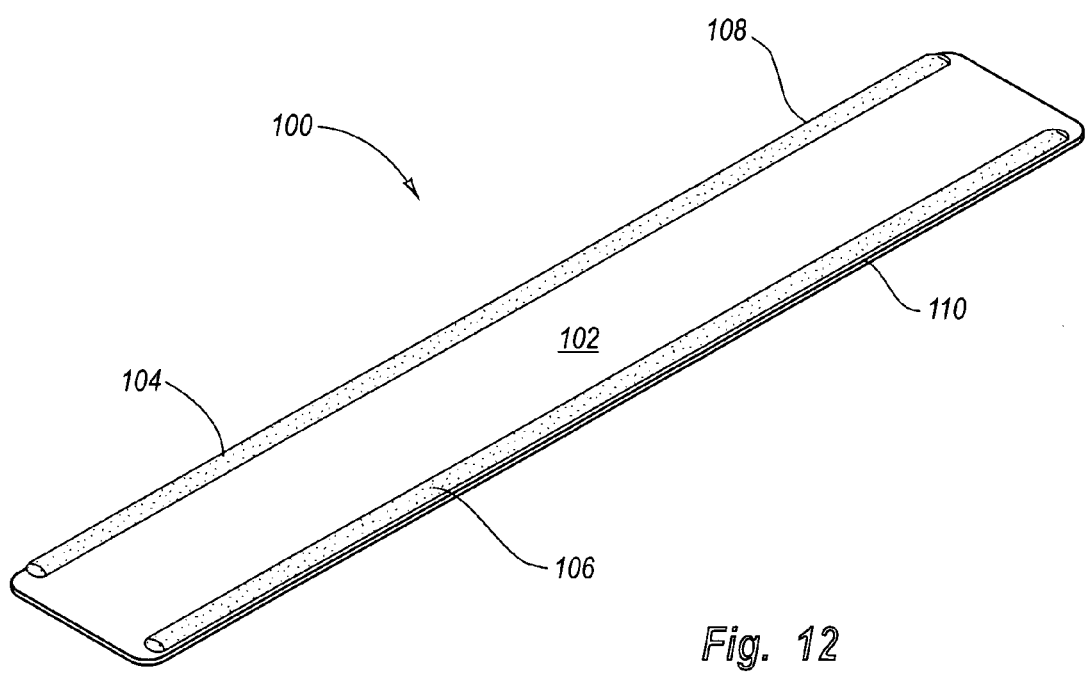
FIG. 12 is a perspective view of an exemplary treatment device according to the invention in the shape of a strip or patch comprising a barrier layer and spaced-apart beads of a protective adhesive composition nearer the front and back edges.

An alternative embodiment of a treatment device in the form of a strip or patch is illustrated in FIG. 12. FIG. 12 is a perspective view of a treatment strip or patch 100 comprising a barrier layer 102, which preferably comprises a moisture-resistant material, a first protective adhesive composition 104, and a second protective adhesive composition or region 106, which together define a space therebetween where a treatment composition (not shown) can be placed prior to use.

A first edge 108 of the treatment strip 100 can be designed so as to terminate at or shy of the labial gingival margin of a person's dental arch when in use. Similarly a second edge 110 can be designed so as to terminate at or shy of the lingual gingival margin of the person's dental arch when in use. Alternatively, one or both of the first and second edges 108, 110 can be designed so as to extend beyond one or both the labial and lingual gingival margins and overlap one or both of the labial and lingual gums. The second edge 110 may alternatively be spaced-apart from the first edge 108 in order to terminate well shy of the lingual gingival margin, or even at or near the occlusal edges of the user's teeth.

Figure 13:
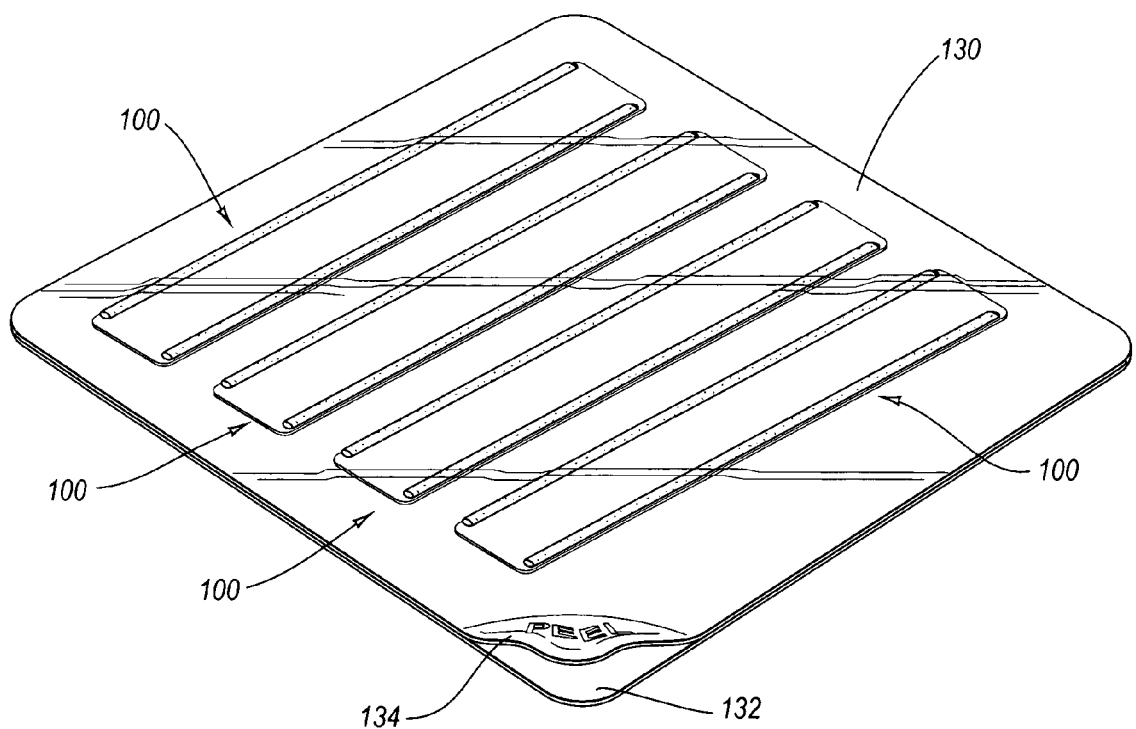
FIG. 13 illustrates multiple treatment strips or patches according to the invention contained within a sealed, protective package having a peelable cover.

In order to protect treatment strips or patches according to the invention from contaminants during storage and prior to use, they can be packaged within a sealed container or package. As illustrated in FIG. 13, one or more treatment strips or patches 100 can be sealed within a protective package 130 that includes a rigid support layer 132 and a peelable cover 134. When it desired to use the treatment strip or patch 100, the peelable cover 134 is removed and the treatment strip 110 is removed or separated from the support layer 132. In addition to, or instead of, the protective package 130, the treatment strip 110 may alternatively include a removable protective layer (not shown) that is temporarily placed adjacent to the protective adhesive composition. When it is desired to use the treatment strip, the removable protective layer is removed so as to expose the adhesive composition.

Figure 14:
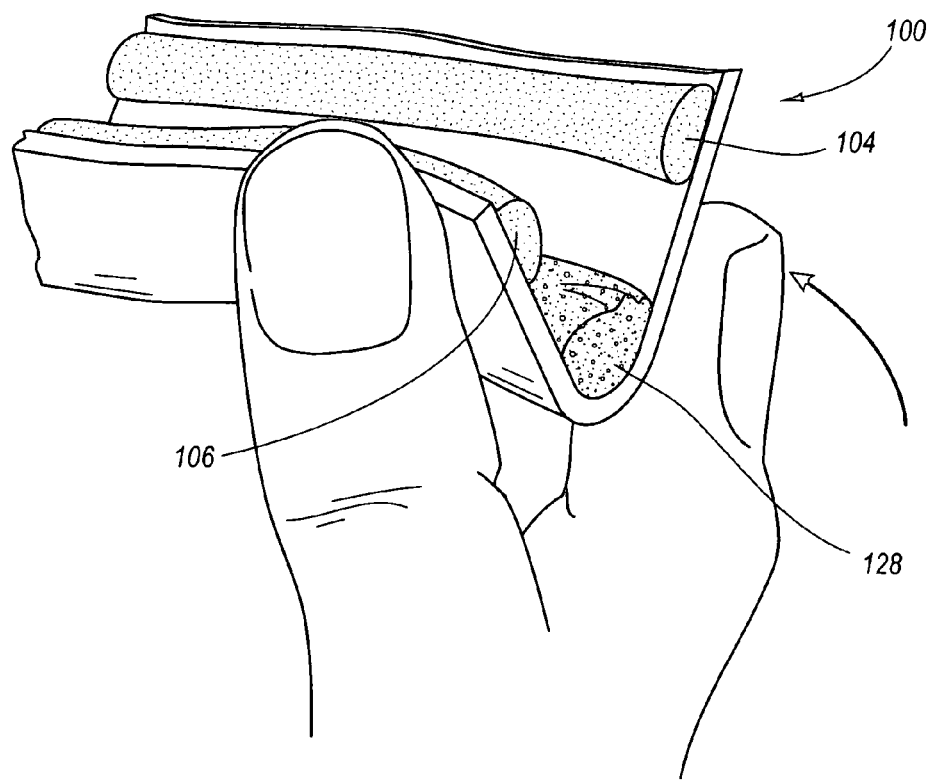
FIG. 14 illustrates an exemplary treatment strip or patch to which a treatment composition has been applied being manipulated so as to have an approximate V-shaped cross section prior to placement over a person's teeth.

FIG. 14 shows a treatment strip or patch 100, after a treatment composition 128 has been applied thereto between the first and second protective adhesive compositions 104 and 106, being optionally manipulated (such as by bending, curving or folding) so as to have an approximate V-shaped cross section in order to facilitate placement of the treatment strip or patch 100 over a person's teeth and/or gums.

Notwithstanding the foregoing examples, it will be appreciated that treatment devices according to the invention can have any profile and longitudinal shape (e.g., they can be flat or have a 3-dimensional shape; they can have a straight or curved longitudinal profile from one end to the other). The front and rear side walls of a tray may define a trough of any desired cross-sectional shape (e.g., the trough can be trapezoidal, rectangular, or any other desired geometric shape).

The size and shape of treatment devices according to the invention can be tailored to readily fit either a person's upper dental arch or lower dental arch. They can be sized so as to treat all or merely a subset of a perso's teeth and/or gums. The treatment devices may be sufficiently flexible so as to readily conform to a wide variety of differently-sized dental arches. The treatment devices may be designed so as to substantially cover the front and lingual surfaces of the teeth to be treated. Treating the front and lingual surfaces helps to treat the interproximal spaces between a person's teeth, although it is certainly within the scope of the invention to treat more of one surface than another.

III. Treatment Kits

Treatment kits according to the invention include one or more treatment devices and one or more initially separate treatment compositions that are applied to the treatment device prior to use. According to one embodiment, one or more treatment compositions are stored and dispensed using one or more unit-dose syringes that contain therein pre-measured doses of the one or more treatment compositions. The use of unit dose syringes helps the user apply the proper amount of treatment composition onto the barrier layer. It also helps prevent overdose in the case where ingestion of the treatment composition may be toxic. The protective adhesive composition further protects the user from ingesting the treatment composition by helping to confine it to a desired location within the user's mouth.

Figure 15:
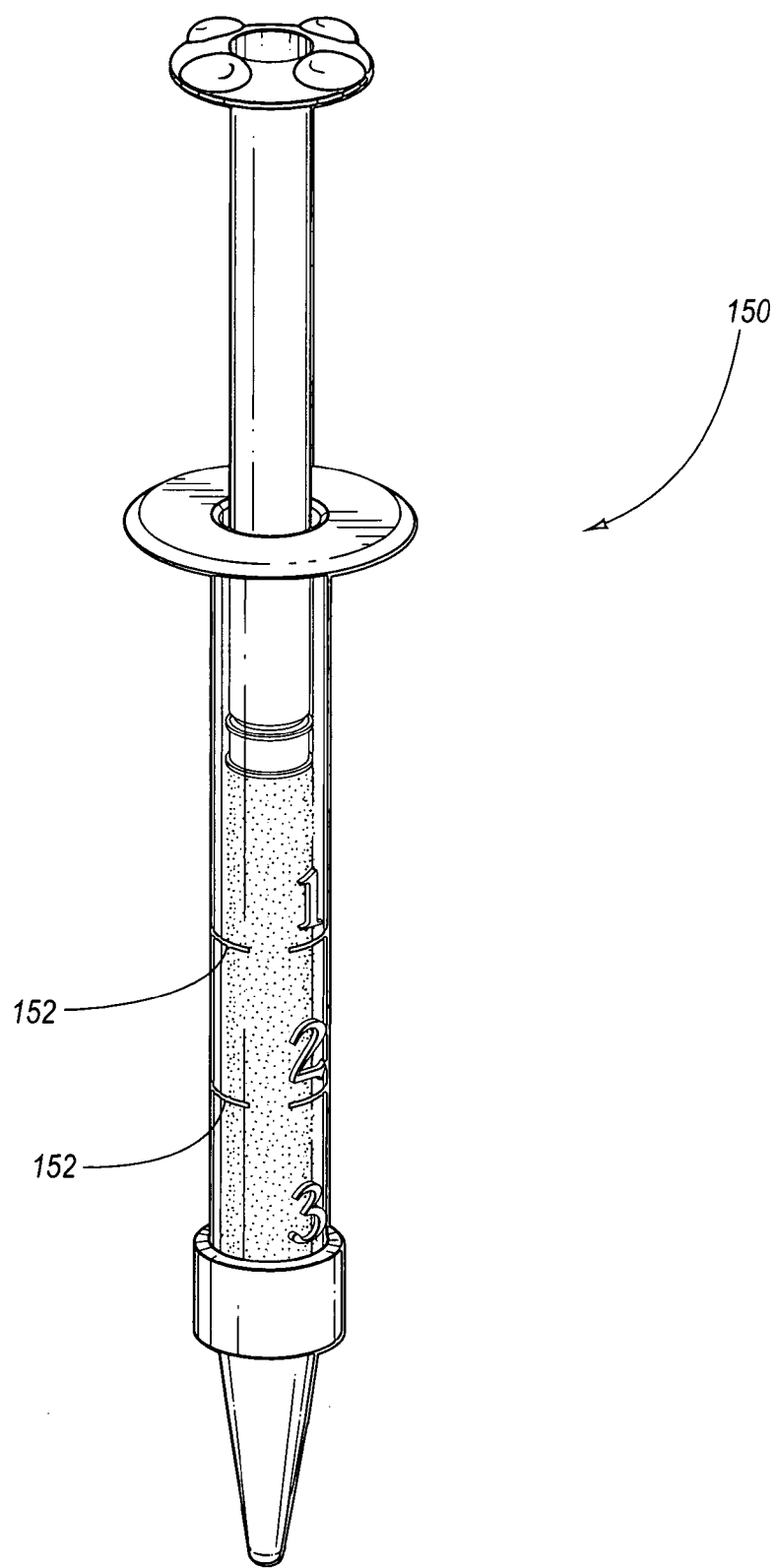
FIG. 15 is a perspective view of a multi-dose syringe for delivering multiple pre-measured doses of a treatment composition.

It is also within the scope of the invention to dispense the treatment composition using a multi-dose syringe. FIG. 15 illustrates an exemplary multi-dose syringe 150 configured to deliver three pre-measured dosages of treatment composition. Graduations 152 provide a visual indicator that helps the user dispense the prescribed amount of treatment composition to the barrier layer.

For convenience of use, multiple treatment devices and syringe-delivery treatment compositions may be packaged together and sold as a kit. In one embodiment, the number of treatment devices provided within each kit equals the number of treatment sessions that represent a prescribed treatment regimen. Because of the ease of placing the inventive treatment devices over a person's teeth, coupled with the reliability with which they remain in place over the teeth, the likelihood that a particular treatment device will fail, or otherwise not work as intended, is greatly diminished compared to conventional bleaching strips.

To efficiently utilize the space within a kit package, multiple treatment devices can be stacked or interested together. The treatment devices can be sealed collectively or individually as desired. A protective package 40 for a treatment tray is depicted in FIG. 7, and a protective package 130 for one or more treatment strips is depicted in FIG. 13. The treatment devices may optionally contain a removable protective layer on an interior surface to shield the protective adhesive composition from contamination or moisture.

IV. Methods of Using Oral Treatment Devices

The treatment devices according to the invention can be designed to be worn for any desired time period. Increasing the concentration of active agent generally reduces the time required to effect the desired treatment. Nevertheless, due to the extremely comfortable fit and reliable adhesion between the inventive treatment devices and the person's teeth, it is possible to wear such devices for extended periods of time in order to ensure more uniform treatment. They may be designed to be worn while performing normal daily activities, such as talking, eating, drinking, smoking, coughing, smiling, frowning, grimacing, or while sleeping. This greatly decreases their intrusiveness into everyday activities compared to conventional bleaching strips, which do not reliably adhere to teeth, or intrusive treatment devices such as large, bulky dental appliances.

The treatment devices according to the invention may be worn over a person's upper dental arch, lower dental arch, or both simultaneously. The ability to reliably and comfortably wear treatment devices over the upper and lower dental arches simultaneously is another departure from bleaching strips, which are not recommended for use in bleaching the upper and lower dental arches at the same time.

Figure 16A:
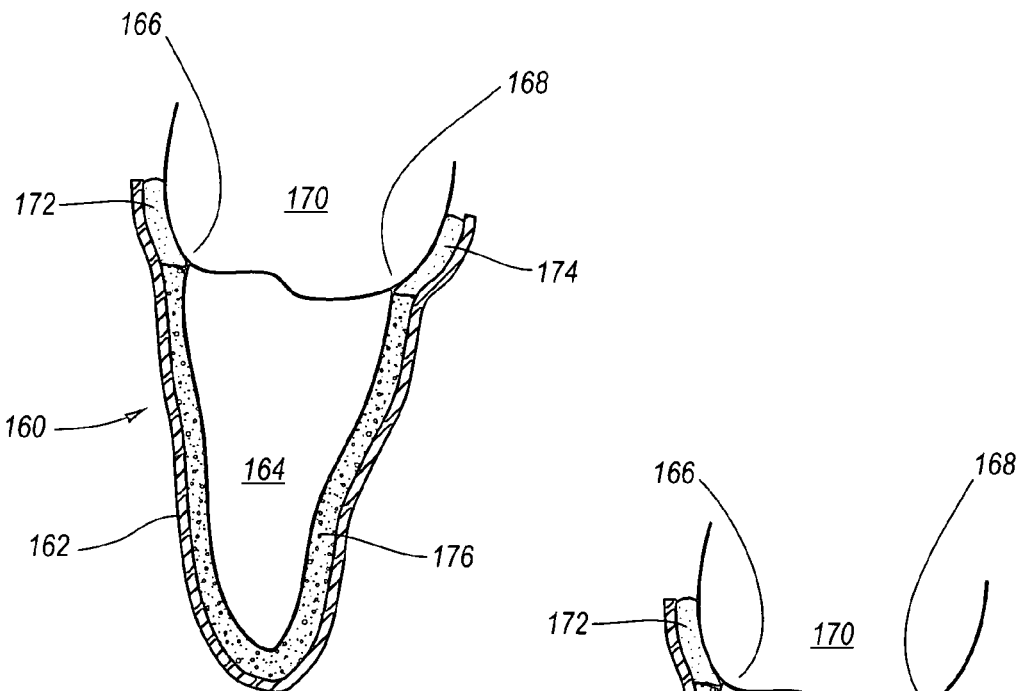
FIG. 16A is a cross-sectional view illustrating a treatment device according to the invention covering the labial and lingual surfaces of a tooth, with a treatment composition in contact with the labial lingual tooth surfaces and a protective adhesive composition in contact with and protecting both the labial and lingual gums at the gingival margin.
Figure 16B:
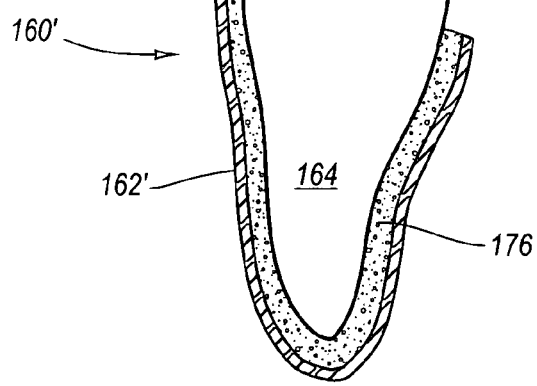
FIG. 16B is a cross-sectional view illustrating a treatment device according to the invention covering the labial surface and part of the lingual surface of a tooth, with a treatment composition in contact with both surfaces and a protective adhesive composition in contact with and protecting the labial gum at the gingival margin.
Figure 16C:
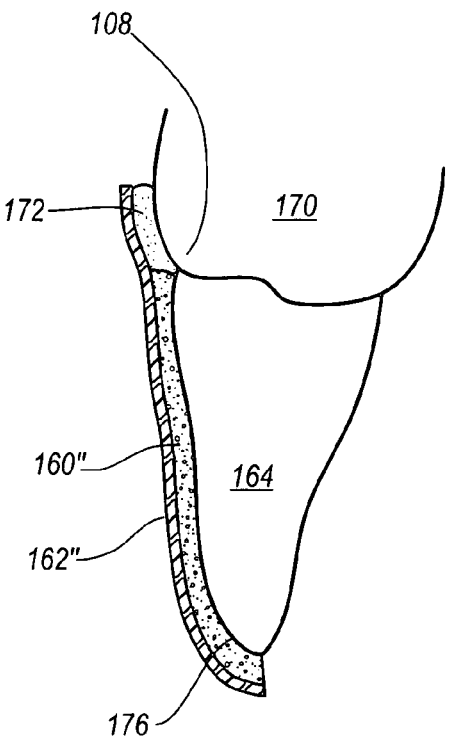
FIG. 16C is a cross-sectional view illustrating a treatment device according to the invention only covering the labial surface of a tooth, with a treatment composition in contact with that surface and a protective adhesive composition in contact with and protecting the labial gum at the gingival margin.

FIG. 5, discussed above, illustrates a person placing a treatment device over the person's upper dental arch. The treatment device can be in the form of a dental tray, strip, patch or other desired shape. As illustrated in FIGS. 16A-16C, the treatment device may cover both surfaces of a person's teeth, all of one surface and part of another surface, or just one surface.

FIG. 16A depicts a treatment device 160 that includes a barrier layer 162 designed so as to cover both the labial and lingual surfaces of a tooth 164, as well as extend beyond the labial and lingual gingival margins 166, 168 of the gum 170. A first protective adhesive composition 172 contacts and adheres to the labial gingival margin 166 and labial surface of the gum 170, and a second protective adhesive composition 174 contacts and adheres to the lingual gingival margin 168 and lingual surface of gum 170. In this way, the first and second protective adhesive compositions 172, 174, in combination with the barrier layer 162, confines a treatment composition 176 to a region between the barrier layer 162 and the labial and lingual surfaces of the tooth 164.

FIG. 16B depicts another embodiment in which a treatment device 160' includes a barrier layer 162' designed to cover all of the labial surface and part of the lingual surface of tooth 164, to extend beyond the labial gingival margin 166, but terminate shy of the lingual gingival margin 168. A protective adhesive composition or region 172 contacts and adheres to the labial gingival margin 166 and labial surface of the gum 170 so as to help confine the treatment composition 176 to the labial surface of tooth 164.

FIG. 16C depicts another embodiment in which a treatment device 160" includes a barrier layer 162" designed so as to only cover the labial surface of tooth 164 and overlap the labial gingival margin 166. A protective adhesive composition or region 172 contacts and adheres to labial gingival margin 166 and labial surface of the gum 170 so as to help confine the treatment composition 176 to the labial surface of tooth 164.

To remove a treatment device, a user can pry open a corner of the barrier layer using a fingernail or rigid tool and then pull the remainder off. Any residual treatment and/or protective adhesive composition that remains adhered to the person's teeth and/or gums can be removed by washing or flushing with water and/or by brushing. Although the inventive treatment and protective adhesive compositions can be very adhesive to teeth and/or gums when protected from excessive moisture, they can be formulated to quickly break down and dissolve when flushed with excess water and/or by gentle mechanical action (e.g., brushing).

The treatment devices can be worn for as little as a few minutes or as long as several hours. By way of example, not limitation, a typical treatment session of fast duration may last from about 10 to about 30 minutes. A treatment session of intermediate duration may last from about 30 minutes to about 2 hours. A treatment session of long duration, including professional treatment or overnight treatment while a person is sleeping, may last from about 2 hours to about 12 hours. Treatment sessions according to the invention may be repeated as many times as needed to obtain a desired degree of treatment.

V. Examples of the Preferred Embodiments

The following are several examples of protective adhesive compositions and treatment compositions for use with the inventive treatment devices of the invention. The exemplary formulations are given by way of example, not by limitation, in order to illustrate compositions that have been found to be useful in treating a person's teeth and/or gums. Unless otherwise indicated, all percentages are by weight.

Example 1

A dental bleaching composition was manufactured by mixing together the following components:

| | |
|---|---|
| Ethanol | 15% |
| Water | 27.9% |
| EDTA Disodium | 0.1% |
| Carbamide Peroxide | 5.0% |
| Carbopol 974 | 5.5% |
| Sodium Hydroxide | 2.15% |
| Glycerine | 32.1% |
| Sucralose | 0.25% |
| Melon Flavoring | 3.0% |
| Melon Color | 0.0012% |
| Polyvinyl Pyrrolidone (>1,000,000 m.w.) | 5.0% |
| Carboxymethyl Cellulose, Sodium | 4.0% |

Example 2

A dental bleaching composition was manufactured by mixing together the following components:

| | |
|---|---|
| Ethanol | 15% |
| Water | 27.9% |
| EDTA Disodium | 0.1% |
| Carbamide Peroxide | 5.0% |
| Carbopol 974 | 5.5% |
| Sodium Hydroxide | 2.15% |
| Glycerine | 35.1% |
| Sucralose | 0.25% |
| Mint Color | 0.004% |
| Polyvinyl Pyrrolidone (>1,000,000 m.w.) | 5.0% |
| Carboxymethyl Cellulose, Sodium | 4.0% |

Example 3

A desensitizing/remineralizing dental bleaching composition was manufactured by mixing together the following components:

| | |
|---|---|
| Water | 33.2% |
| EDTA Disodium | 0.1% |
| Sodium Fluoride | 0.25% |
| Potassium Nitrate | 0.5% |
| Carbamide Peroxide | 11.0% |
| Hydrogen Peroxide | 6.8% |
| Sucralose | 0.25% |
| Glycerine | 27.45% |
| Carbopol 974 | 5.5% |
| Sodium Hydroxide 50% solution | 2.5% |
| Melon Flavoring | 3.0% |
| Sodium Laurel Sulfate | 0.2% |
| Polyvinyl Pyrrolidone (>1,000,000 m.w.) | 5% |
| Carboxy Methyl Cellulose, Sodium | 4% |

Example 4

| | |
|---|---|
| Water | 33.2% |
| EDTA Disodium | 0.1% |
| Sodium Fluoride | 0.25% |
| Potassium Nitrate | 0.5% |
| Carbamide Peroxide | 11.0% |
| Hydrogen Peroxide | 6.8% |
| Sucralose | 0.25% |
| Glycerine | 29.85% |
| Carbopol 974 | 5.5% |
| Sodium Hydroxide 50% solution | 2.5% |
| Mint Flavoring | 0.6% |
| Sodium Laurel Sulfate | 0.2% |
| Polyvinyl Pyrrolidone (>1,000,000 m.w.) | 5% |
| Carboxy Methyl Cellulose, Sodium | 4% |

Example 5

A dental bleaching composition was manufactured by mixing together the following components:

| | |
|---|---|
| Water | 33.55% |
| EDTA Disodium | 0.1% |
| Sodium Laurel Sulfate | 0.1% |
| BHT | 0.1% |
| Hydrogen Peroxide | 10.5% |
| Sucralose | 0.25% |
| Glycerine | 40.2% |
| Carbopol 974 | 5.3% |
| Sodium Hydroxide | 2.3% |
| Polyvinyl Pyrrolidone (>1,000,000 m.w.) | 3% |
| Carboxy Methyl Cellulose | 4% |
| Natural Peppermint Oil | 0.6% |

Example 6

A substantially solid dental bleaching composition was formed by mixing together the following components and then removing a substantial portion of the water and ethanol by evaporation:

| | |
|---|---|
| Carbamide Peroxide | 7.1% |
| Kollidon 90 (M.W. = 1.3 million) | 25% |
| Water | 10.7% |
| Ethanol | 50.7% |
| Glycerin | 2.9% |
| Aerosil 200 | 3.6% |

Example 7

A dental desensitizing/remineralizing gel composition was formed by mixing together the following components:

| | |
|---|---|
| Sodium Fluoride | 0.25% |
| Polyvinyl pyrrolidone (M.W. = 1.3 million) | 30% |
| Water | 69.75% |

The foregoing desensitizing/remineralizing composition is either used as a gel or else formed into a substantially solid composition by removing a substantial portion of the water by evaporation.

Example 8

A dental desensitizing gel composition was formed by mixing together the following components:

| | |
|---|---|
| Sodium Citrate | 5% |
| Polyvinyl pyrrolidone (M.W. = 1.3 million) | 20% |
| Water | 75% |

The foregoing desensitizing composition is either used as a gel or else formed into a substantially solid composition by removing a substantial portion of the water by evaporation.

Example 9

A dental desensitizing gel composition was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The foregoing desensitizing composition is either used as a gel or else formed into a substantially solid composition by removing a substantial portion of the solvent by evaporation.

Example 10

A dental desensitizing/remineralizing gel composition was formed by mixing together the following components:

| | |
|---|---|
| Potassium Nitrate | 0.5% |
| Sodium Fluoride | 0.25% |
| Polyvinyl pyrrolidone (M.W. = 1.3 million) | 32% |
| Ethanol | 30% |
| Water | 37.25% |

The foregoing desensitizing/remineralizing composition is either used as a gel or else formed into a substantially solid composition by removing a substantial portion of the solvent by evaporation.

Example 11

A dental desensitizing/remineralizing gel composition was formed by mixing together the following components:

| | |
|---|---|
| Potassium Nitrate | 0.5% |
| Sodium Fluoride | 0.25% |
| Carbamide Peroxide | 15% |
| Polyvinyl pyrrolidone (M.W. = 1.3 million) | 33% |
| Water | 51.25% |

The foregoing desensitizing/remineralizing composition is either used as a gel or else formed into a substantially solid composition by removing a substantial portion of the water by evaporation.

Example 12

An antimicrobial gel composition was formed by mixing together the following components:

| | |
|---|---|
| Chlorhexidine Gluconate | 2% |
| Polyvinyl pyrrolidone (M.W. = 1.3 million) | 30% |
| Ethanol | 33% |
| Water | 35% |

The foregoing antimicrobial composition is either used as a gel or else formed into a substantially solid composition by removing a substantial portion of the solvent by evaporation.

Example 13

An antimicrobial gel composition was formed by mixing together the following components:

| | |
|---|---|
| Cetylpyridinium Chloride | 2% |
| Ethanol | 28% |
| Polyvinyl pyrrolidone (M.W. = 1.3 million) | 35% |
| Water | 35% |

The foregoing antimicrobial composition is either used as a gel or else formed into a substantially solid composition by removing a substantial portion of the water by evaporation.

Example 14

An antimicrobial gel composition was formed by mixing together the following components:

| | |
|---|---|
| Phenol | 3% |
| Polyvinyl pyrrolidone (M.W. = 1.3 million) | 35% |
| Ethanol | 62% |

The foregoing antimicrobial composition is either used as a gel or else formed into a substantially solid composition by removing a substantial portion of the ethanol by evaporation.

Example 15

A protective adhesive gel composition was formed by mixing together the following components:

| | |
|---|---|
| Water | 25% |
| Ethanol | 30% |
| Glycerin | 10% |
| Polyvinyl pyrrolidone (M.W. = 1.3 million) | 30% |
| Aerosil 200 | 5% |

The foregoing protective adhesive composition is either used as a gel or else formed into a substantially solid composition by removing a substantial portion of the solvent by evaporation.

Example 16

A protective adhesive gel composition was formed by mixing together the following components:

| | |
|---|---|
| Water | 20% |
| Ethanol | 30% |
| Glycerin | 15% |
| Polyvinyl pyrrolidone (M.W. = 1.3 million) | 30% |
| Aerosil 200 | 5% |

The foregoing protective adhesive composition is either used as a gel or else formed into a substantially solid composition by removing a substantial portion of the solvent by evaporation.

Example 17

A protective adhesive gel composition was formed by mixing together the following components:

| | |
|---|---|
| Water | 20% |
| Ethanol | 40% |
| Glycerin | 10% |
| Polyvinyl pyrrolidone (M.W. = 1.3 million) | 30% |

The foregoing protective adhesive composition is either used as a gel or else formed into a substantially solid composition by removing a substantial portion of the solvent by evaporation.

Example 18

A protective adhesive gel composition was formed by mixing together the following components:

| | |
|---|---|
| Ethanol | 60.6% |
| Glycerin | 5.1% |
| Polyvinyl pyrrolidone (M.W. = 1.3 million) | 30% |
| Aerosil 200 | 4.3% |

The foregoing protective adhesive composition is either used as a gel or else formed into a substantially solid composition by removing a substantial portion of the ethanol by evaporation.

Example 19

A protective adhesive gel composition was formed by mixing together the following components:

| | |
|---|---|
| Ethanol | 61.9% |
| Glycerin | 9.5% |
| Polyvinyl pyrrolidone (M.W. = 1.3 million) | 23.8% |
| Aerosil 200 | 4.8% |

The foregoing protective adhesive composition is either used as a gel or else formed into a substantially solid composition by removing a substantial portion of the ethanol by evaporation.

Example 20

A protective adhesive gel composition was formed by mixing together the following components:

| | |
|---|---|
| Ethanol | 63.6% |
| Glycerin | 9.1% |
| Polyvinyl pyrrolidone (M.W. = 1.3 million) | 27.3% |

The foregoing protective adhesive composition is either used as a gel or else formed into a substantially solid composition by removing a substantial portion of the ethanol by evaporation.

Example 21

A protective adhesive gel composition was formed by mixing together the following components:

| | |
|---|---|
| Ethanol | 44% |
| Polyvinyl pyrrolidone (M.W. = 1.3 million) | 34% |
| Glycerin | 14% |
| Sodium Lauryl Sulfate | 3% |
| Sucralose | 1% |
| Artificial Peach Flavor | 4% |

The foregoing protective adhesive composition is either used as a gel or else formed into a substantially solid composition by removing a substantial portion of the ethanol by evaporation.

Example 22

A desensitizing/remineralizing gel composition was formed by mixing together the following components:

| | |
|---|---|
| Ethanol | 31.95% |
| Water | 10% |
| Polyvinyl pyrrolidone (M.W. > 1 million) | 27% |
| Polyvinyl pyrrolidone (M.W. ≈ 60,000) | 10% |
| Sodium Lauryl Sulfate | 0.5% |
| Glycerin | 15% |
| Sucralose (25% solution) | 0.5% |
| Peach Flavor | 4% |
| Potassium Nitrate | 0.8% |
| Sodium Fluoride | 0.25% |

The foregoing desensitizing/remineralizing composition is either used as a gel or else formed into a substantially solid composition by removing a substantial portion of the solvent by evaporation.

Example 23

A dental bleaching composition was formed by mixing together the following components:

| | |
|---|---|
| Carboxy Methyl Cellulose (sodium salt) | 2% |
| Carbamide Peroxide | 22.5% |
| Glycerin | 28% |
| Water | 16.4% |
| Sodium Saccharine Powder | 2% |
| Sodium EDTA | 0.1% |
| Cabosil M-5 (SiO$_2$) | 7% |
| Peach Flavor | 2% |
| Polyethylene Glycol (M.W. = 20,000) | 20% |

Example 24

A dental bleaching composition was formed by mixing together the following components:

| | |
|---|---|
| Water | 19.2% |
| Edetate Disodium | 0.1% |
| Carbamide Peroxide | 18.5% |
| Xylitol C | 7% |
| Glycerin | 25.4% |
| CARBOPOL 974 | 5.3% |
| NaOH (50% in water) | 4.5% |
| Carboxy Methyl Cellulose | 4% |
| Kollidon 90F | 10% |
| Peach Flavor | 3% |
| Sucralose (25% in water) | 3% |

Example 25

A dental bleaching composition was formed by mixing together the following components:

| | |
|---|---|
| Water | 18% |
| Edetate Disodium | 0.1% |
| Carbamide Peroxide | 18.5% |
| Sucralose (25% in water) | 3% |
| Glycerin | 41.6% |
| CARBOPOL 974 | 5.3% |
| NaOH (50% in water) | 4.5% |
| Kollidon 90F | 2% |
| Carboxy Methyl Cellulose | 4% |
| Peach Flavor | 3% |

Example 26

A dental bleaching composition was formed by mixing together the following components:

| | |
|---|---|
| Water | 18% |
| EDTA | 0.1% |
| Carbamide Peroxide | 22% |
| Sucralose (25% in water) | 2% |
| Glycerin | 37.1% |
| CARBOPOL 974 | 5.3% |
| NaOH (50% in water) | 4.5% |
| Kollidon 90F | 2% |
| Carboxy Methyl Cellulose | 5% |
| Peach Flavor | 4% |

Example 27

A dental bleaching composition was formed by mixing together the following components:

| | |
|---|---|
| Water | 18% |
| EDTA | 0.1% |
| Carbamide Peroxide | 22% |
| Sucralose (25% in water) | 2% |
| Glycerin | 40.1% |
| CARBOPOL 974 | 5.3% |
| NaOH (50% in water) | 4.5% |
| Kollidon 90F | 2% |
| Carboxy Methyl Cellulose | 5% |
| Peppermint Oil | 1% |

Example 28

A dental bleaching composition was formed by mixing together the following components:

| | |
|---|---|
| Water | 22.5% |
| EDTA | 0.1% |
| Carbamide Peroxide | 18.5% |
| Sucralose (25% in water) | 0.75% |
| Glycerin | 41.6% |
| CARBOPOL 974 | 5.3% |
| NaOH (50% in water) | 2.25% |
| Polyvinyl Pyrrolidone (M.W. > 1 million) | 2% |
| Carboxy Methyl Cellulose | 4% |
| Flavor (peach, watermelon or peppermint) | 3% |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oral treatment device adapted for placement over a person's teeth, comprising:
    a barrier layer comprised of a moisture-resistant material and being sized and configured for placement over a person's teeth, said barrier layer having an inner surface, an outer surface, and at least one rim or outer periphery; and
    a hydrophilic protective adhesive composition positioned over a portion of said inner surface of said barrier layer at or near said at least one rim or outer periphery, said protective adhesive composition comprising at least one hydrophilic tissue adhesion agent that includes at least one hydrophilic polymer,
        wherein a substantial portion of said inner surface of said barrier layer remains uncovered by said protective adhesive composition so as to permit placement of a treatment composition onto and into direct contact with said inner surface of said barrier layer,
        wherein said protective adhesive composition is readily adhesive to moist oral tissues,
        wherein said protective adhesive composition is positioned at or near said at least one rim or outer periphery of said barrier layer so as to contact at least one of a user's gingival margin or gums during use and so that said protective adhesive composition, in combination with said barrier layer, is adapted to at least partially confine a treatment composition when positioned adjacent to and in direct contact with said inner layer of said barrier layer to a desired location on the user's teeth and/or gums during use.

2. An oral treatment device as defined in claim 1, said barrier layer being flexible so as to readily conform to the shape of a person's dental arch during use.

3. An oral treatment device as defined in claim 1, said barrier layer comprising at least one moisture-resistant material selected from the group consisting of wax, metal foil, paraffin, ethylene-vinyl acetate copolymer, ethylene-vinyl alcohol copolymer, polycaprolactone, polyolefin, polyethylene, high density polyethylene, low density polyethylene, ultra-low density polyethylene, polypropylene, polytetrafluoroethylene, polyester, polycarbonate, polyurethane, polyamide, or polyesteramide.

4. An oral treatment device as defined in claim 1, said barrier layer having a cross-sectional thickness in a range of about 0.025 mm to about 1.5 mm.

5. An oral treatment device as defined in claim 1, said barrier layer having a cross-sectional thickness in a range of about 0.05 mm to about 1 mm.

6. An oral treatment device as defined in claim 1, said barrier layer having a tray-like configuration comprising at least two sidewalls that define an interior volume within which said protective adhesive composition is positioned prior to use.

7. An oral treatment device as defined in claim 6, said barrier layer having a horse-shoe configuration prior to use so as to approximate the curvature of a person's dental arch, said interior volume remaining empty, except for said protective adhesive composition, and free of obstruction prior to introducing a treatment composition therein.

8. An oral treatment device as defined in claim 6, at least a portion of said barrier layer having a cross section that is approximately U-shaped, V-shaped, L-shaped, rectangular, or trapezoidal.

9. An oral treatment device as defined in claim 6, said barrier layer being sufficiently thin and flexible so as to be unable to maintain said tray-like configuration absent external support, the oral treatment device further comprising a removable exoskeleton that maintains said barrier layer in said tray-like configuration prior to use.

10. An oral treatment device as defined in claim 1, said barrier layer comprising a strip or patch prior to use.

11. An oral treatment device as defined in claim 1, said barrier layer designed so as to approximately terminate at or near a person's gingival margin during use.

12. An oral treatment device as defined in claim 1, said barrier layer designed so as to overlap a person's gingival margin during use.

13. An oral treatment device as defined in claim 1, said protective adhesive composition comprising at least two spaced-apart beads defining a space therebetween for placement of a treatment composition prior to use, one of said spaced-apart beads being positioned at or near a rim or outer periphery that is adapted to lie adjacent to or near a person's labial gingival tissue and another of said spaced-apart beads being positioned at or near a rim or outer periphery on an opposite side of said barrier layer that is adapted to lie adjacent to or near a person's lingual gingival tissue when the oral treatment device is placed over the person's teeth.

14. An oral treatment device as defined in claim 1, said protective adhesive composition further comprising a liquid or gel carrier so that said protective adhesive composition is a sticky and viscous gel.

15. An oral treatment device as defined in claim 1, said protective adhesive composition being substantially solid prior to use and becoming highly adhesive to teeth or gums when moistened with saliva or water.

16. An oral treatment device as defined in claim 1, wherein said hydrophilic tissue adhesion agent comprises at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

17. An oral treatment device as defined in claim 1, said protective adhesive composition further comprising at least one member selected from the group comprising dental bleaching agents, dental desensitizing agents, remineralizing agent, antimicrobial agents, preservatives, antiplaque agents, anti-tartar agents, gingival soothing agents, anesthetics, antioxidants, flavorants, mouth freshening agents, detergents, and colorants.

18. An oral treatment device as defined in claim 1, further comprising a treatment composition on and in direct contact with said inner surface of said barrier layer and being positioned so that said adhesive composition, in combination with said barrier layer, at least partially confines said treatment composition to a desired location on the user's teeth and/or gums.

19. An oral treatment device as defined in claim 18, said treatment composition comprising at least one tissue adhesion agent and at least one active agent.

20. An oral treatment device as defined in claim 19, said treatment composition further comprising a liquid or gel carrier so that said treatment composition is a sticky and viscous gel.

21. An oral treatment device as defined in claim 19, said treatment composition being substantially solid prior to use and becoming highly adhesive to teeth when moistened with saliva or water.

22. An oral treatment device as defined in claim 19, said tissue adhesion agent within said treatment composition comprising at least one of polyvinyl pyrrolidone (PVP), carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaceharide gum, or protein.

23. An oral treatment device as defined in claim 19, said active agent comprising at least one member selected from the group comprising dental bleaching agents, dental desensitizing agents, remineralizing agents, antimicrobial agents, antiplaque agents, anti-tartar agents, gingival soothing agents, anesthetics, antioxidants, and mouth freshening agents.

24. An oral treatment device as defined in claim 1, further comprising a sealed package within which the oral treatment device is sealed prior to use.

25. An oral treatment device as defined in claim 1, further comprising a removable exoskeleton adjacent to said outer surface of said barrier layer that maintains said barrier layer in a desired shape prior to use.

26. An oral treatment device as defined in claim 25, said removable exoskeleton maintaining said barrier layer in the desired shape of a dental tray prior to use.

27. A kit for use in providing a desired oral treatment, comprising:
an oral treatment device according to any one of claims 1-17 or 24-26; and
at least one treatment composition initially separate from said oral treatment device,
wherein said at least one treatment composition contains an active agent,
wherein said protective adhesive composition of said oral treatment devices contains either (a) no active agent or (b) less active agent than said oral treatment composition.

28. A kit for use in providing a desired oral treatment, comprising:
an oral treatment device according to claim 1; and
at least one treatment composition initially contained within a syringe,
wherein said at least one treatment composition contains an active agent,
wherein said protective adhesive composition of said oral treatment devices contains either (a) no active agent or (b) less active agent than said oral treatment composition.

29. A kit as defined in claim 28, wherein said treatment composition is contained within a unit dose syringe.

30. A kit as defined in claim 28, wherein said treatment composition is contained within a multi-dose syringe comprising graduations that provide a visual indication of individual doses or portions thereof.

31. A method for providing a desired oral treatment, comprising:
(a) obtaining a kit comprised of;
(i) an oral treatment composition initially contained within a syringe, wherein said oral treatment composition contains an active agent; and
(ii) an oral treatment device comprising:
a barrier layer comprised of a moisture-resistant material and being sized and configured for placement over a person's teeth, said barrier layer having an inner surface, an outer surface, and at least one rim or outer periphery; and
a hydrophilic protective adhesive composition positioned over a portion of said inner surface of said barrier layer at or near said at least one rim or outer periphery, said protective adhesive composition comprising at least one hydrophilic tissue adhesion agent that includes at least one hydrophilic polymer, wherein a substantial portion of said inner surface of said barrier layer remains uncovered by said protective adhesive composition so as to permit placement of said oral treatment composition onto and into direct contact with said inner surface of said barrier layer, wherein said protective adhesive composition is readily adhesive to moist oral tissues, wherein said protective adhesive composition is positioned at or near said at least one rim or outer periphery of said barrier layer so as to contact at least one of a user's gingival margin or gums during use and so that said protective adhesive composition, in combination with said barrier layer, is adapted to at least partially confine said oral treatment composition when positioned adjacent to and in direct contact with said inner layer of said barrier layer to a desired location on the user's teeth and/or gums during use, wherein said protective adhesive composition on said barrier layer contains either (1) no active agent or (2) less active agent than said oral treatment composition;
(b) dispensing said oral treatment composition from said syringe directly onto said barrier layer at a location other than on said protective adhesive composition; and
(c) placing said oral treatment device over at least one of a person's teeth or gums for a desired period of time.

32. A kit for use in providing a desired oral treatment, comprising:
an oral treatment device comprised of:
a barrier layer comprised of a moisture-resistant material and being sized and configured for placement over a person's teeth, the barrier layer having an inner surface, an outer surface, and at least one rim or outer periphery; and
a hydrophilic protective adhesive composition comprising at least one hydrophilic tissue adhesion agent and positioned on only a portion of said inner surface of said barrier layer at or near said at least one rim or outer periphery so as to contact at least one of a user's gingival margin or gums during use, wherein said protective adhesive composition is readily adhesive to moist oral tissues and, except for said protective adhesive composition, said inner layer of said barrier layer remaining uncovered and unobstructed so as to permit ready placement of a treatment composition onto and into direct contact with said inner surface of said barrier layer; and
a treatment composition, completely separate and detached from said oral treatment device and adapted for placement into direct contact with said barrier layer, comprising at least one tissue adhesion agent and at least one active agent.

33. A kit as defined in claim 32, said tissue adhesion agent within said protective adhesion composition comprising at least one hydrophilic polymer.

34. A kit as defined in claim 32, wherein said treatment composition is contained within a unit dose syringe.

35. A kit as defined in claim 32, wherein said treatment composition is contained within a multi-dose syringe comprising graduations that provide a visual indication of individual doses or portions thereof.

36. A kit as defined in claim 32, said treatment composition comprising an insert for a dental tray.

37. A kit for use in providing at least one oral treatment, comprising:
an oral treatment composition preloaded within a syringe and formulated so as to provide at least one oral treatment; and
a moisture-resistant barrier layer having in inner surface to which a hydrophilic protective adhesive composition has been applied, said protective adhesive composition being applied to only a portion of said inner surface at or near a rim or outer periphery of said barrier layer, a portion of said inner layer of said barrier layer remaining uncovered by said protective adhesive composition so as to permit ready placement of said oral treatment composition onto and into direct contact with said inner surface of said barrier layer,
wherein said moisture-resistant barrier layer is sized and configured so as to fit over a person's teeth and gingival margin in order to protect said oral treatment composition and protective adhesive composition from saliva or moisture during use,
wherein said hydrophilic protective adhesive composition includes a hydrophilic tissue adhesion agent so as to readily adhere to moist oral tissue and, in combination with said moisture-resistant barrier layer, help confines said treatment composition, when placed onto said inner surface of said barrier layer, to a desired location in a person's mouth during use.

38. A method of manufacturing a kit for use in providing a desired oral treatment, comprising:
preparing an oral treatment device by positioning a hydrophilic protective adhesive composition comprising at least one hydrophilic tissue adhesion agent onto a portion of an inner surface of a moisture-resistant barrier layer at or near a rim or outer periphery of said barrier layer so that said protective adhesive composition contacts at least one of a user's gingival margin or gums when said barrier layer is placed over a person's teeth during use, wherein said protective adhesive composition is readily adhesive to moist oral tissues, a portion of said inner layer of said barrier layer remaining uncovered by said protective adhesive composition so as to permit ready placement of an oral treatment composition onto and into direct contact with said inner surface of said barrier layer; and
providing an oral treatment composition that is completely separate and detached from said oral treatment device and contained within a syringe prior to use for application directly to, and so as to make direct contact with, said inner surface of said barrier layer.

* * * * *

UNITED STATES PATENT AND TRADEMARK OFFICE
CERTIFICATE OF CORRECTION

PATENT NO.       : 7,625,210 B2　　　　　　　　　　　　　　　　　　　　　　Page 1 of 1
APPLICATION NO. : 10/914487
DATED            : December 1, 2009
INVENTOR(S)      : Allred et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 790 days.

Signed and Sealed this

Twenty-sixth Day of October, 2010

David J. Kappos
*Director of the United States Patent and Trademark Office*